(12) United States Patent
Cote et al.

(10) Patent No.: US 7,731,691 B2
(45) Date of Patent: Jun. 8, 2010

(54) SUBCUTANEOUS INFUSION DEVICE AND DEVICE FOR INSERTION OF A CANNULA OF AN INFUSION DEVICE AND METHOD

(75) Inventors: Steve Cote, Stillwater, MN (US); James Marrs, Arden Hills, MN (US); Mark Faust, Lino Lakes, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 630 days.

(21) Appl. No.: 10/705,719

(22) Filed: Nov. 10, 2003

(65) Prior Publication Data
US 2005/0101932 A1    May 12, 2005

(51) Int. Cl.
*A61M 5/178* (2006.01)

(52) U.S. Cl. .................................................... 604/158

(58) Field of Classification Search .............. 604/506, 604/158, 136, 164.01, 131, 134, 500
See application file for complete search history.

(56) References Cited

U.S. PATENT DOCUMENTS

| | | | |
|---|---|---|---|
| 3,547,119 A | 12/1970 | Hall et al. | |
| 4,378,015 A | 3/1983 | Wardlaw | |
| 4,531,937 A | 7/1985 | Yates | |
| 4,755,173 A | 7/1988 | Konopka et al. | |
| 4,994,042 A | 2/1991 | Vadher | |
| 5,092,853 A | 3/1992 | Couvertier, II | |
| 5,129,884 A | 7/1992 | Dysarz | |
| 5,135,496 A | 8/1992 | Vetter | |
| 5,135,502 A | 8/1992 | Koenig, Jr. | |
| 5,137,516 A | 8/1992 | Rand et al. | |
| 5,176,650 A | 1/1993 | Haining | |
| 5,176,662 A | 1/1993 | Bartholomew et al. | |
| 5,248,301 A | 9/1993 | Koenig, Jr. | |
| 5,257,980 A | 11/1993 | Van Antwerp et al. | |
| 5,451,210 A | 9/1995 | Kramer et al. | |
| 5,522,803 A | 6/1996 | Teissen-Simony | |
| 5,545,143 A | 8/1996 | Fischell | |
| 5,573,510 A | 11/1996 | Isaacson | |

(Continued)

FOREIGN PATENT DOCUMENTS

DE    299 05 072 U1    9/1999

(Continued)

*Primary Examiner*—Nicholas D Lucchesi
*Assistant Examiner*—Christopher D Koharski
(74) *Attorney, Agent, or Firm*—Merchant & Gould P.C.

(57) ABSTRACT

An infusion device including a site and a set for delivery of a substance to a patient. The site can include a cannula that is introduced into a subcutaneous layer of skin of the patient. The set can be coupled to the site by placing the set over the site and moving the set from an unlocked to a locked position. The set can be oriented at multiple rotational orientations with respect to the site, and can be coupled and uncoupled with the site multiple times. Also included is a device for inserting a subcutaneous infusion device into a subcutaneous layer of skin of a patient. Some devices automatically retract a needle used to introduce the cannula. Upon full introduction of the needle and associated cannula of the subcutaneous infusion device into a subcutaneous layer of skin of a patient, the device can move the needle into a retracted state.

8 Claims, 36 Drawing Sheets

U.S. PATENT DOCUMENTS

| | | | |
|---|---|---|---|
| 5,575,777 A | 11/1996 | Cover et al. |
| 5,584,813 A | 12/1996 | Livingston et al. |
| 5,591,188 A | 1/1997 | Waisman |
| 5,676,156 A | 10/1997 | Yoon |
| 5,738,641 A | 4/1998 | Watson |
| 5,817,058 A | 10/1998 | Shaw |
| 5,833,666 A | 11/1998 | Davis |
| 5,848,990 A | 12/1998 | Cirelli et al. |
| 5,851,197 A | 12/1998 | Marano et al. |
| 5,968,011 A | 10/1999 | Larsen et al. |
| 5,980,506 A | 11/1999 | Mathiasen |
| 6,017,328 A | 1/2000 | Fischell et al. |
| 6,056,718 A | 5/2000 | Funderburk et al. |
| 6,056,726 A | 5/2000 | Isaacson |
| 6,077,244 A | 6/2000 | Botich et al. |
| 6,086,575 A | 7/2000 | Mejslov |
| 6,093,172 A | 7/2000 | Funderburk et al. |
| 6,123,690 A | 9/2000 | Mejslov |
| 6,159,181 A | 12/2000 | Crossman et al. |
| 6,293,925 B1 | 9/2001 | Safabash et al. |
| 6,302,866 B1 | 10/2001 | Marggi |
| 6,355,021 B1 | 3/2002 | Nielsen et al. |
| 6,450,992 B1 | 9/2002 | Cassidy, Jr. |
| 6,520,938 B1 | 2/2003 | Funderburk et al. |
| 6,572,586 B1 | 6/2003 | Wojcik |
| 6,579,267 B2 | 6/2003 | Lynch et al. |
| 6,607,509 B2 | 8/2003 | Bobroff et al. |
| 6,620,136 B1 | 9/2003 | Pressly, Sr. et al. |
| 6,685,674 B2 | 2/2004 | Douglas et al. |
| 6,736,797 B1 * | 5/2004 | Larsen et al. ........ 604/167.05 |
| 6,749,589 B1 | 6/2004 | Douglas et al. |
| 6,830,562 B2 | 12/2004 | Mogensen et al. |
| 6,926,694 B2 | 8/2005 | Morano-Ford |
| 7,018,344 B2 | 3/2006 | Bressler et al. |
| 7,052,483 B2 | 5/2006 | Wojcik |
| 7,056,302 B2 | 6/2006 | Douglas |
| 2001/0039387 A1 | 11/2001 | Rutynowski |
| 2001/0053889 A1 | 12/2001 | Marggi et al. |
| 2002/0045867 A1 | 4/2002 | Nielsen et al. |
| 2002/0077599 A1 | 6/2002 | Wojcik |
| 2002/0161332 A1 | 10/2002 | Ramey |
| 2002/0173769 A1 | 11/2002 | Gray et al. |
| 2003/0014018 A1 | 1/2003 | Giambattista et al. |
| 2003/0060781 A1 | 3/2003 | Mogensen et al. |
| 2003/0109829 A1 * | 6/2003 | Mogensen et al. ..... 604/164.01 |
| 2003/0125669 A1 | 7/2003 | Safabash et al. |
| 2003/0130619 A1 | 7/2003 | Safabash et al. |
| 2003/0158520 A1 | 8/2003 | Safabash et al. |
| 2003/0199823 A1 | 10/2003 | Bobroff et al. |
| 2003/0225373 A1 | 12/2003 | Bobroff et al. |
| 2003/0225374 A1 | 12/2003 | Mathiasen |
| 2004/0002682 A1 | 1/2004 | Kovelman et al. |
| 2004/0143216 A1 | 7/2004 | Douglas et al. |
| 2004/0158207 A1 * | 8/2004 | Hunn et al. ............ 604/164.01 |
| 2004/0199123 A1 | 10/2004 | Nielsen |
| 2004/0204687 A1 | 10/2004 | Mogensen et al. |
| 2004/0215151 A1 | 10/2004 | Marshall et al. |
| 2004/0236284 A1 | 11/2004 | Hoste et al. |
| 2004/0260250 A1 | 12/2004 | Harris et al. |
| 2005/0043687 A1 | 2/2005 | Mogensen et al. |
| 2005/0075606 A1 | 4/2005 | Botich et al. |
| 2005/0101910 A1 | 5/2005 | Bowman et al. |
| 2005/0101933 A1 | 5/2005 | Marrs |
| 2005/0107743 A1 | 5/2005 | Fangrow, Jr. |
| 2005/0131346 A1 | 6/2005 | Douglas |
| 2006/0041224 A1 | 2/2006 | Jensen |
| 2006/0173413 A1 | 8/2006 | Fan |

FOREIGN PATENT DOCUMENTS

| | | |
|---|---|---|
| DE | 202 20 543 U1 | 10/2003 |
| EP | 0 290 176 A1 | 4/1988 |
| EP | 0 451 040 A1 | 3/1991 |
| EP | 0 239 244 B1 | 9/1991 |
| EP | 0 615 768 B1 | 12/1999 |
| WO | WO 96/32981 | 10/1996 |
| WO | WO 02/081012 A2 | 10/2002 |
| WO | WO 02/102442 A1 | 12/2002 |

* cited by examiner

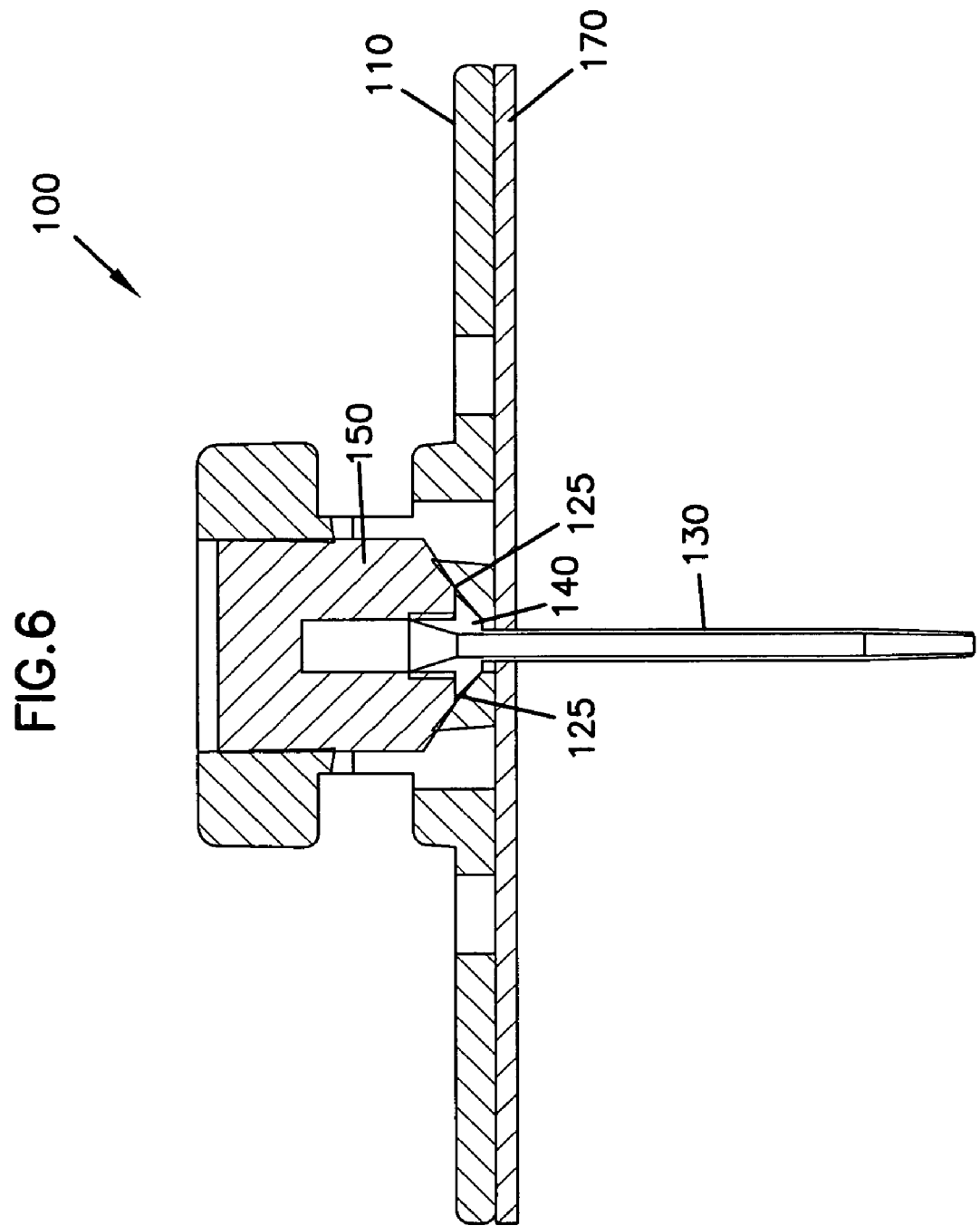

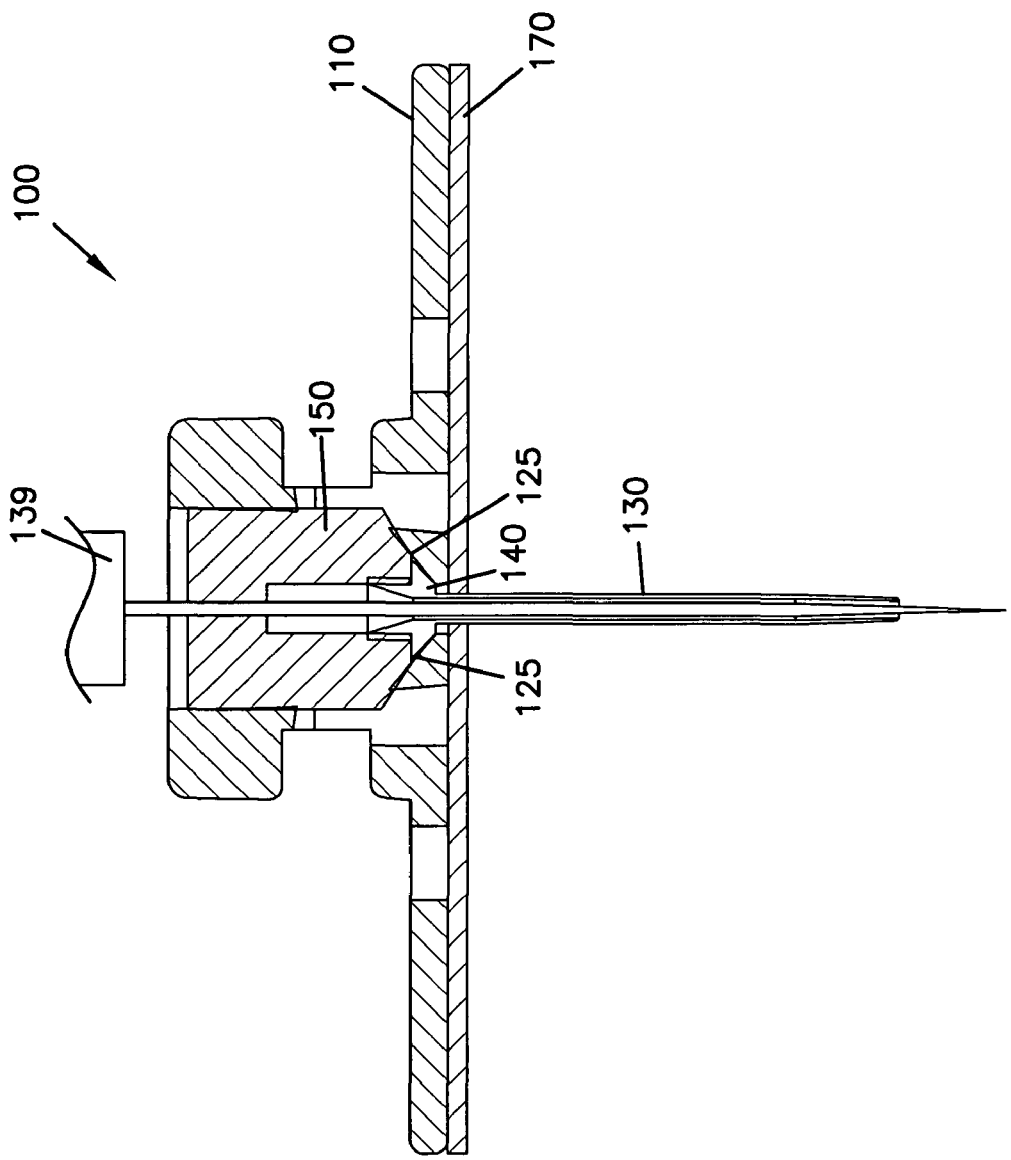

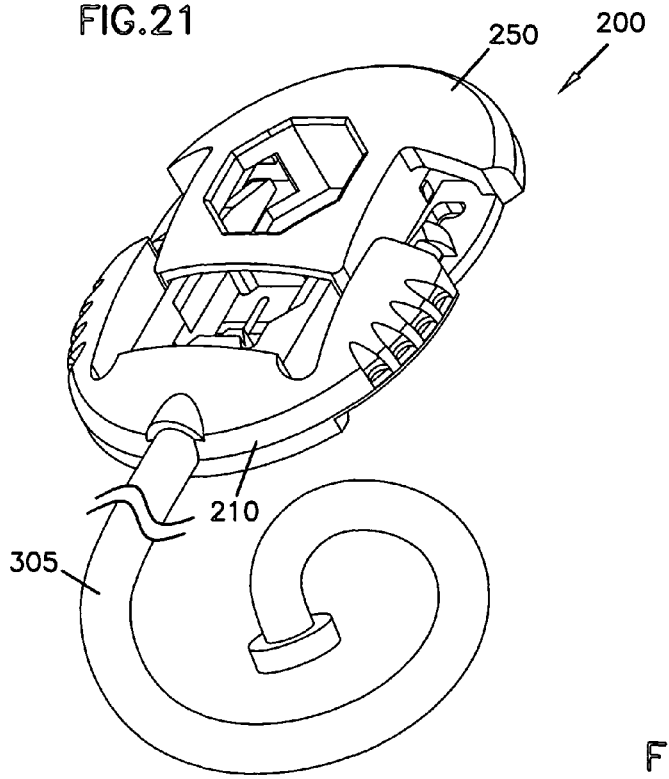
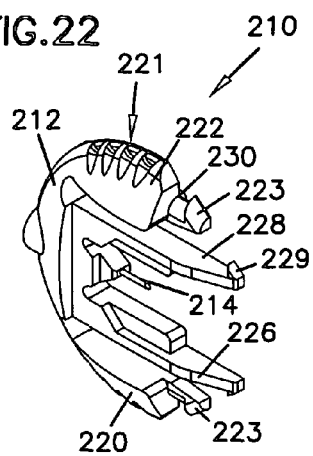
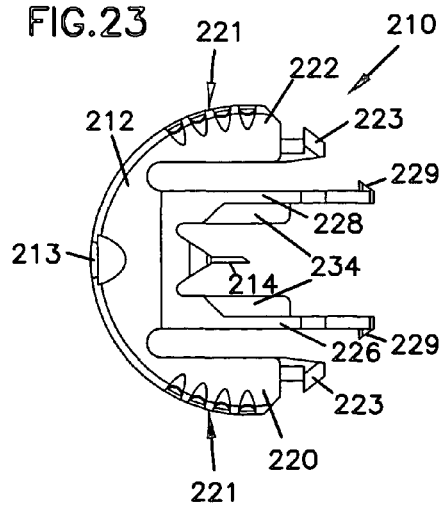
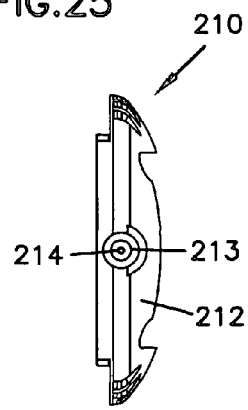
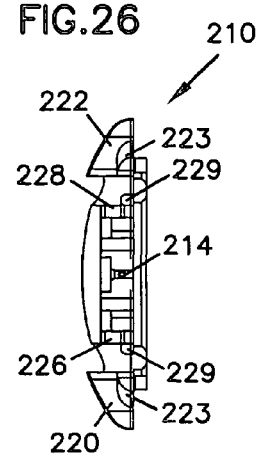

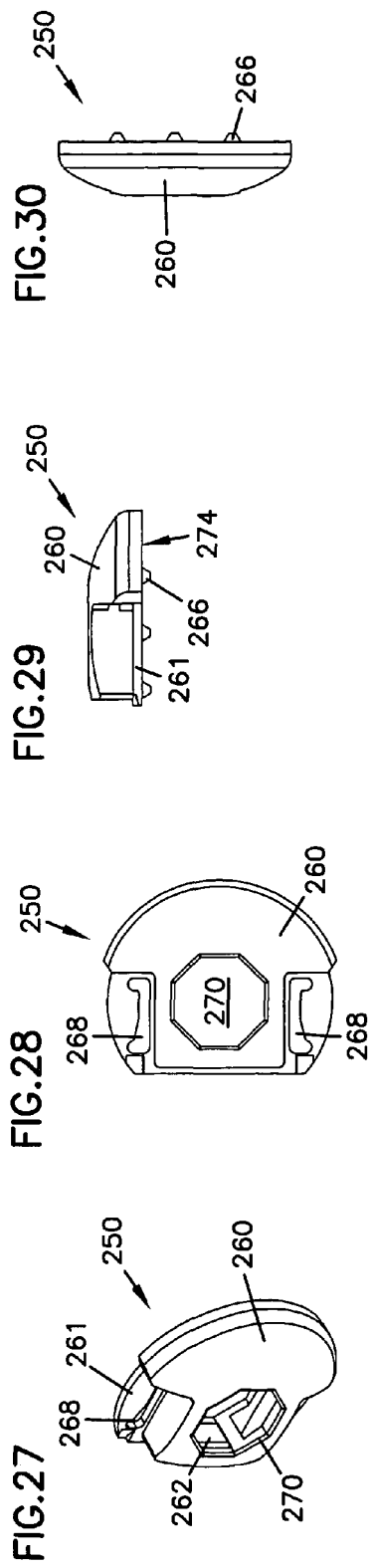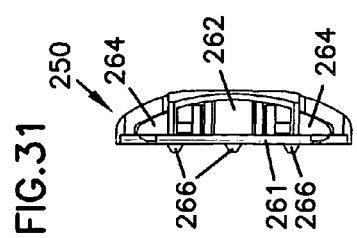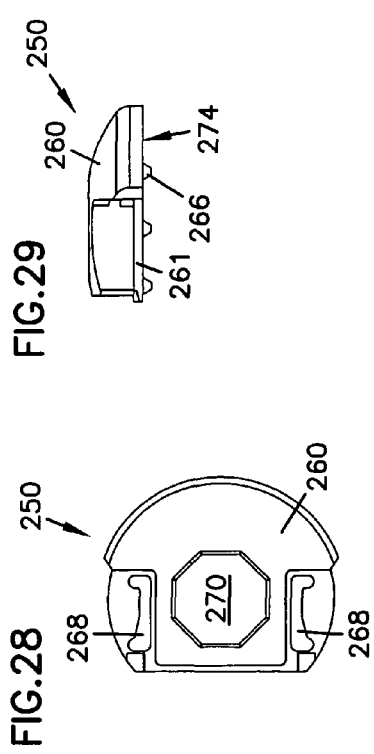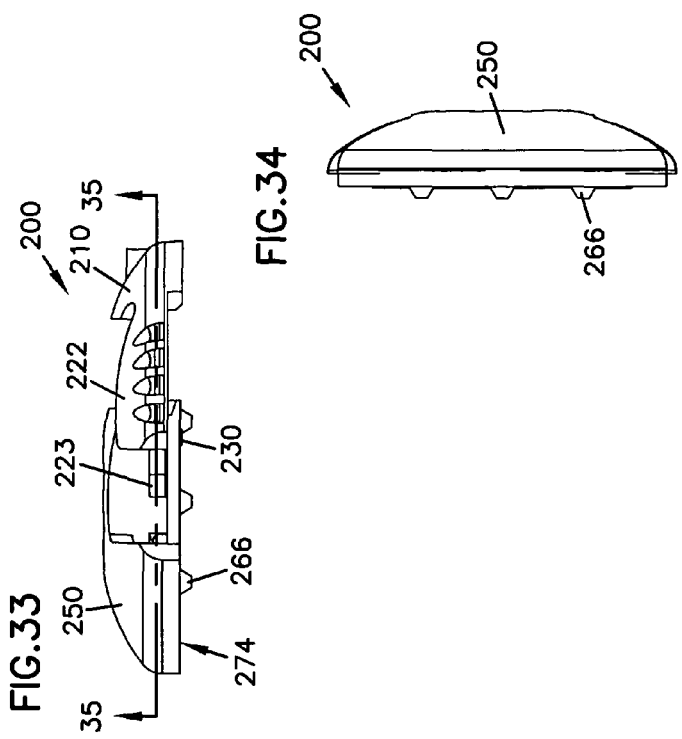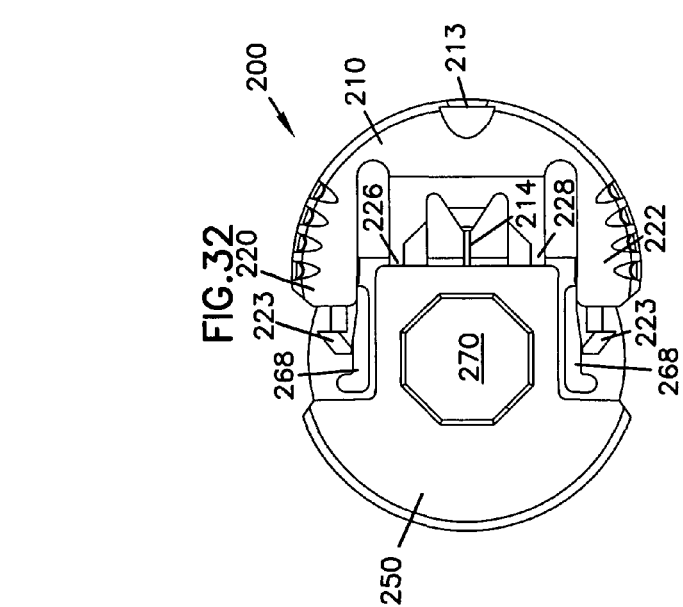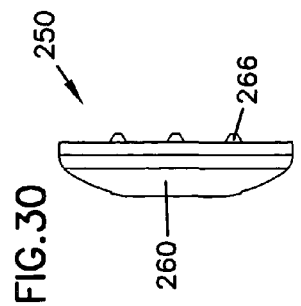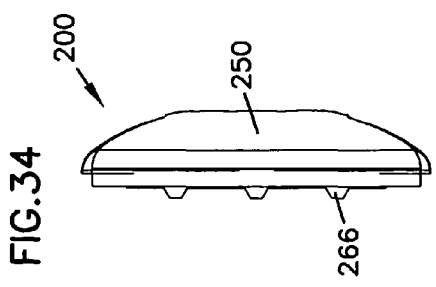

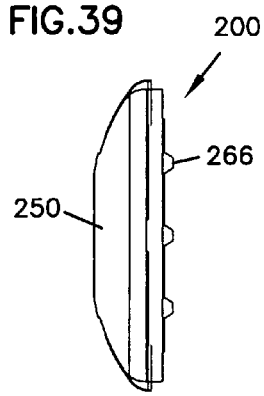
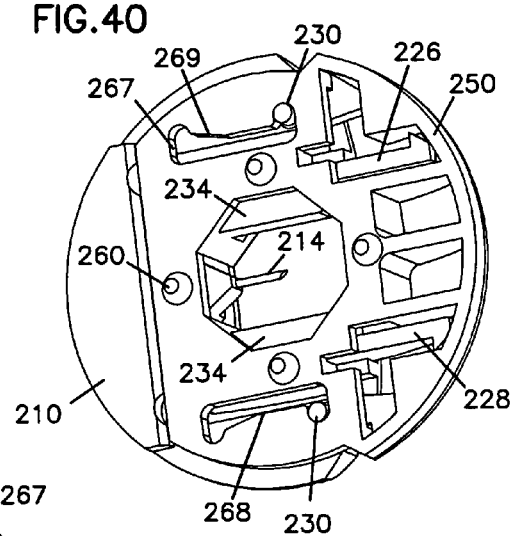
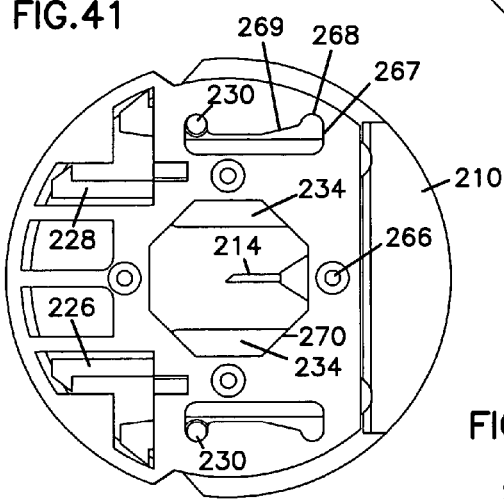
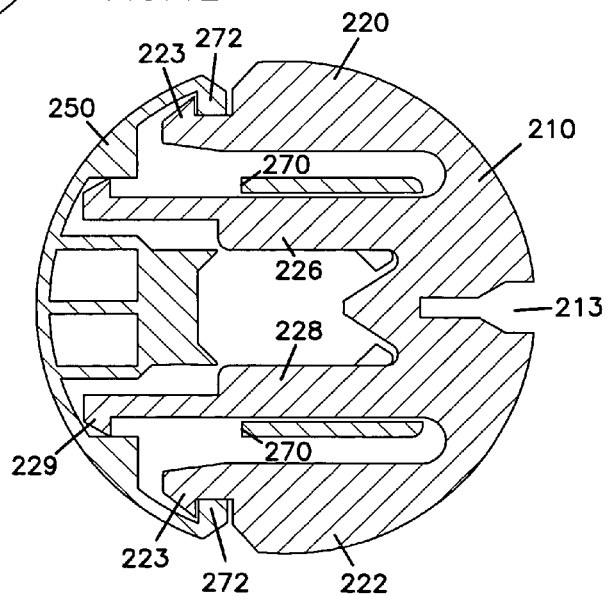

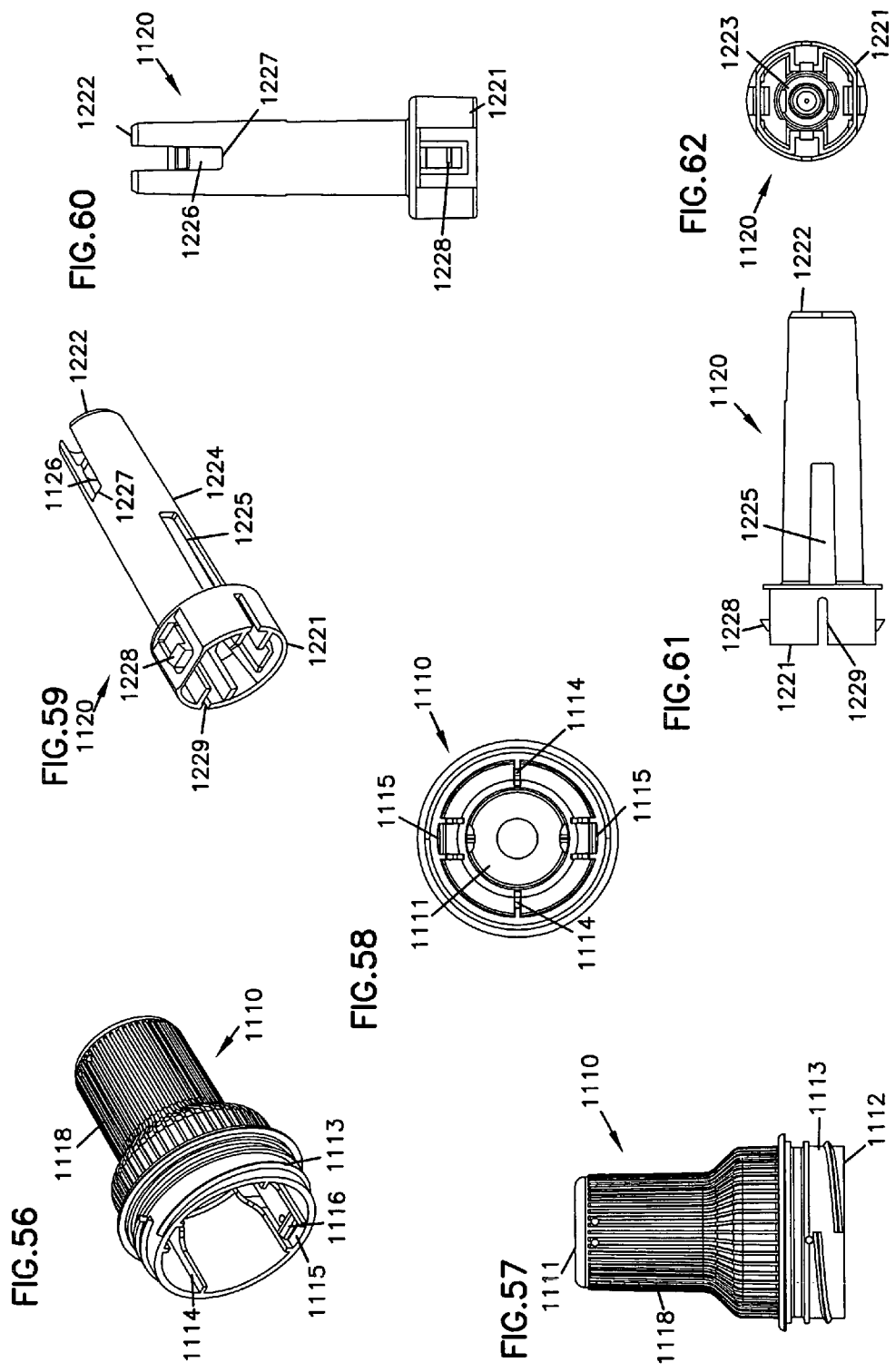

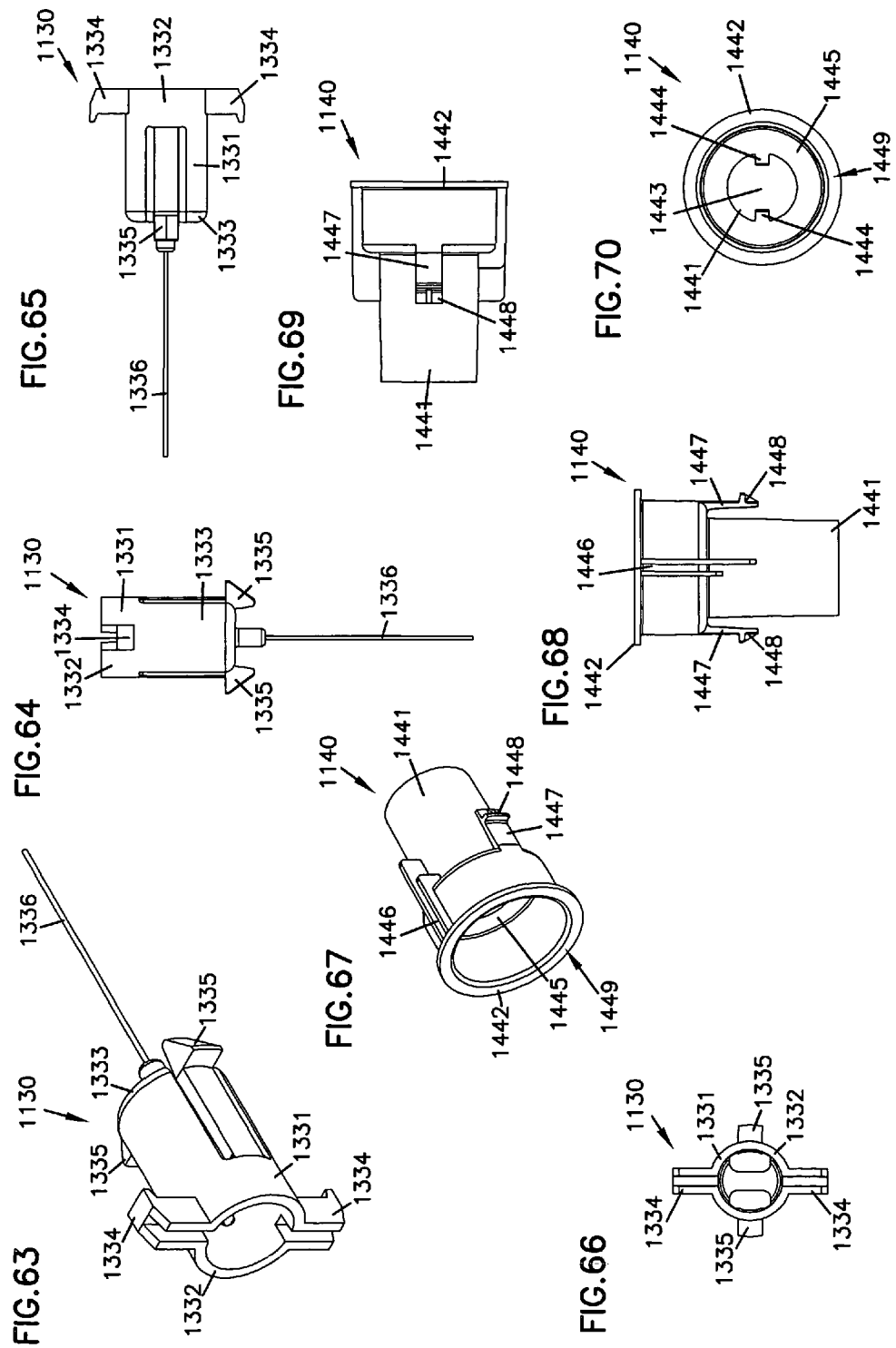

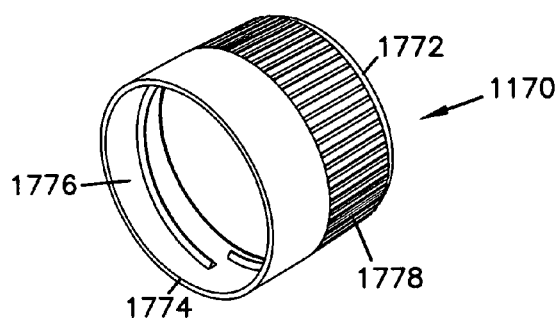
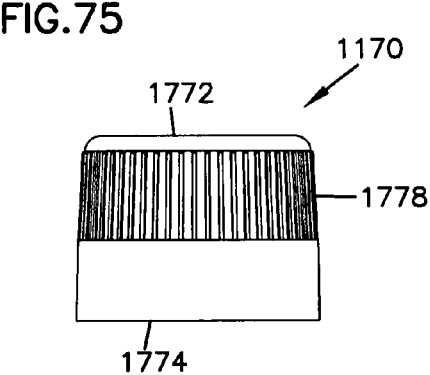
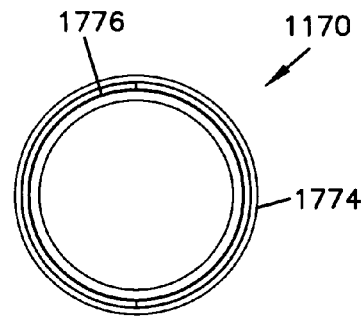
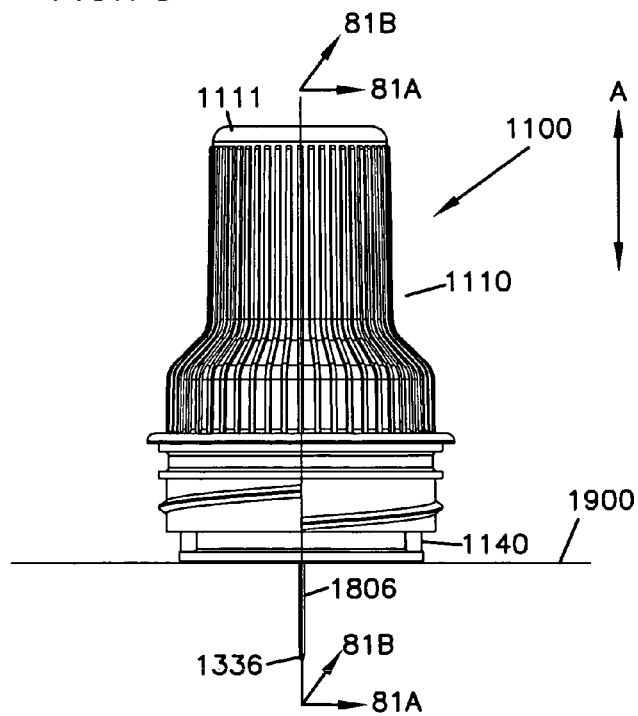
FIG.74
FIG.75
FIG.76
FIG.77
FIG.78

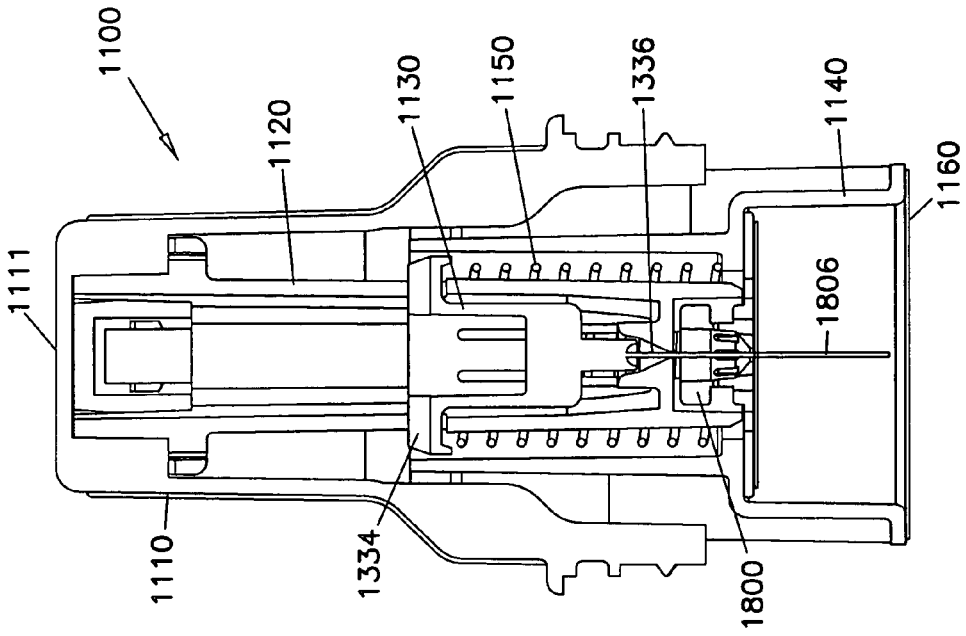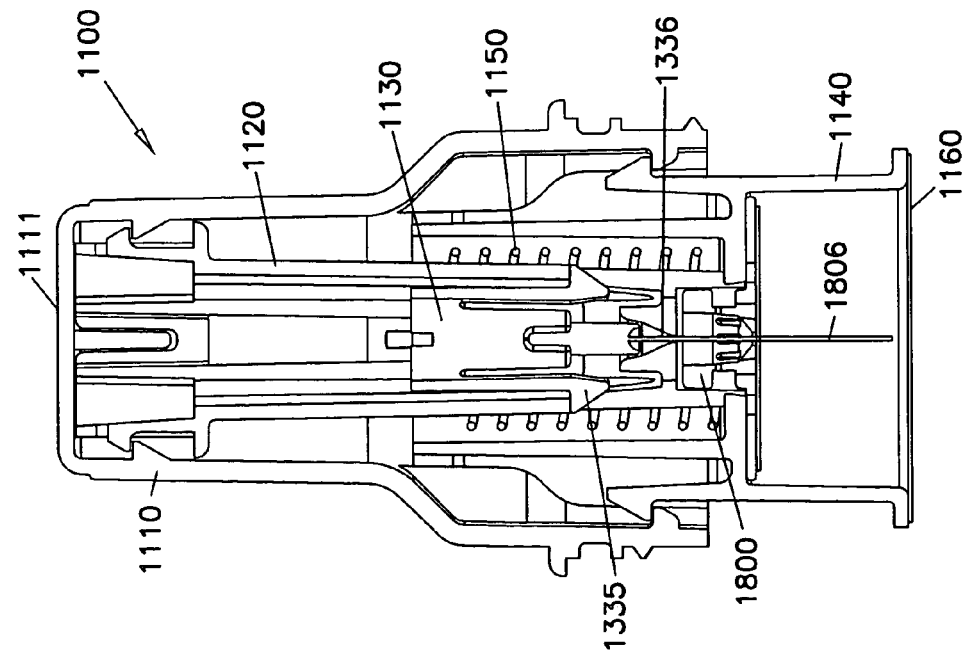

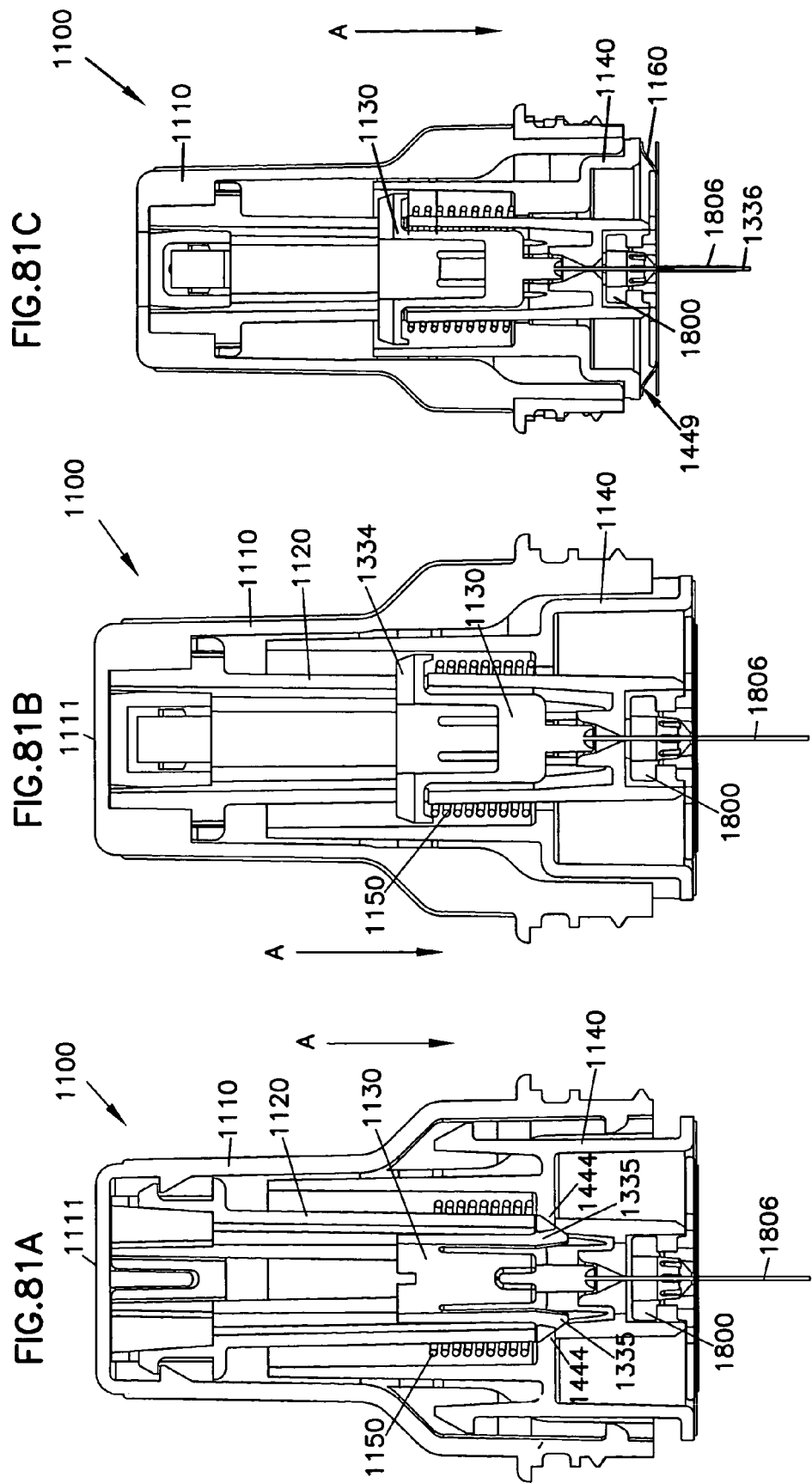

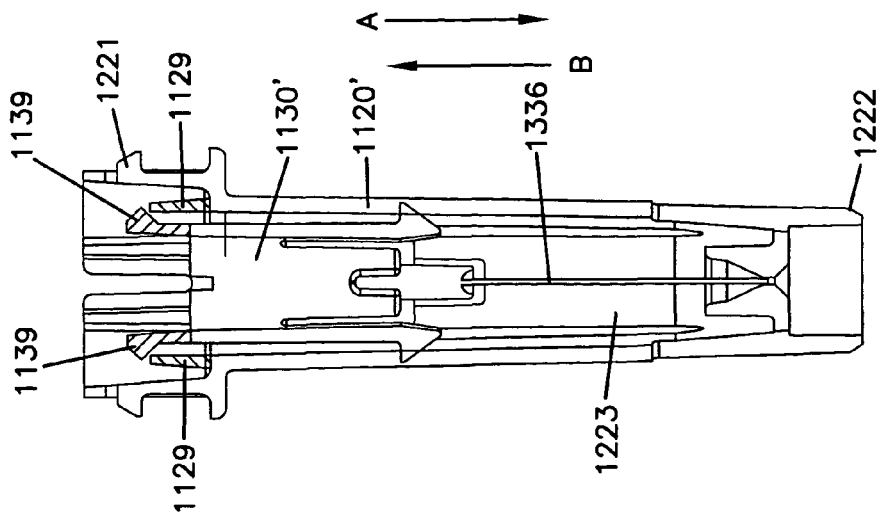
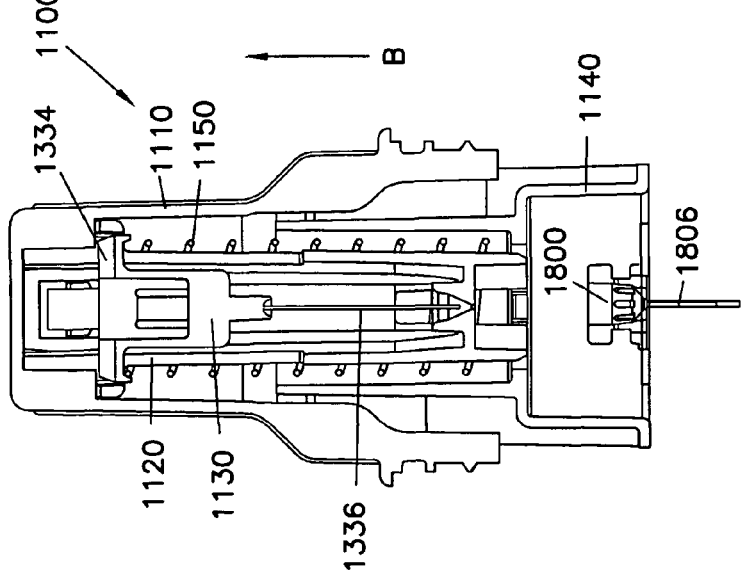
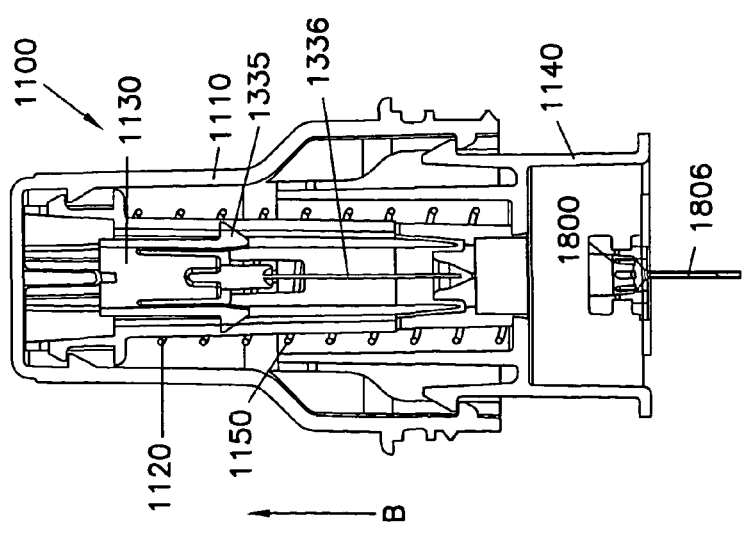

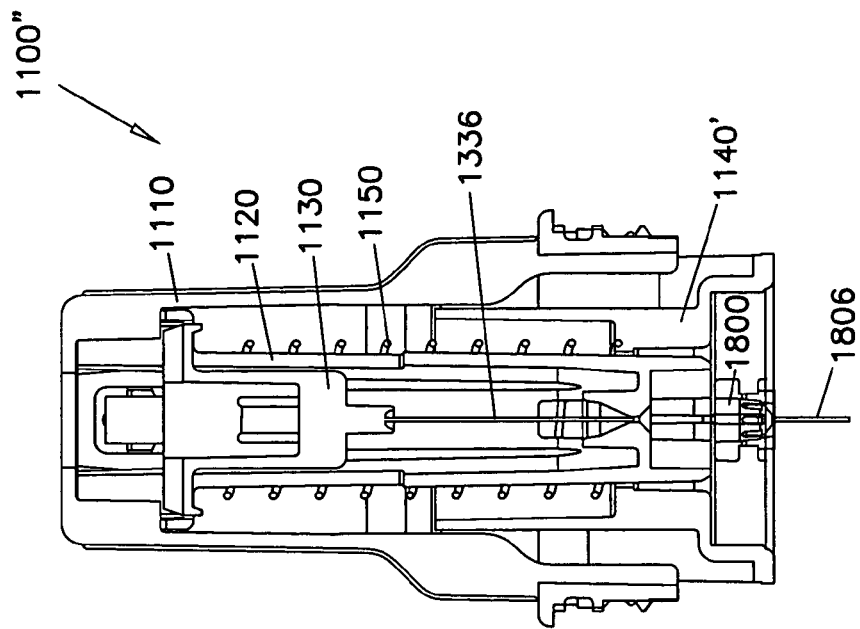
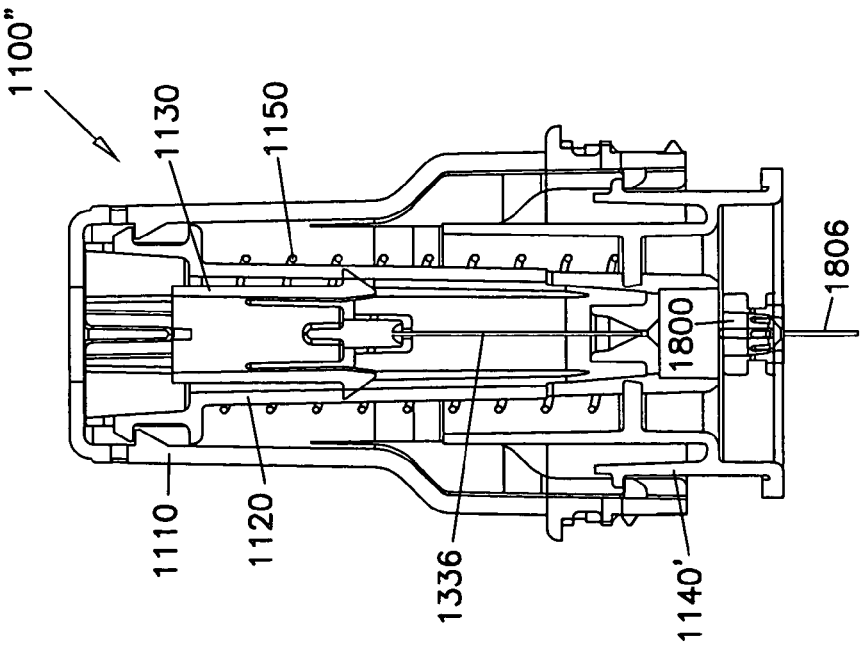

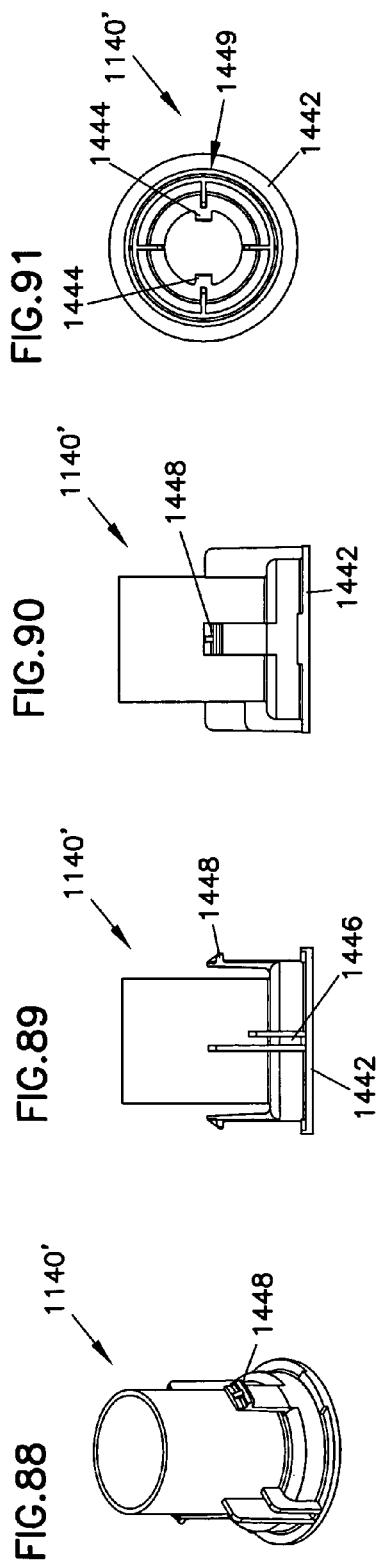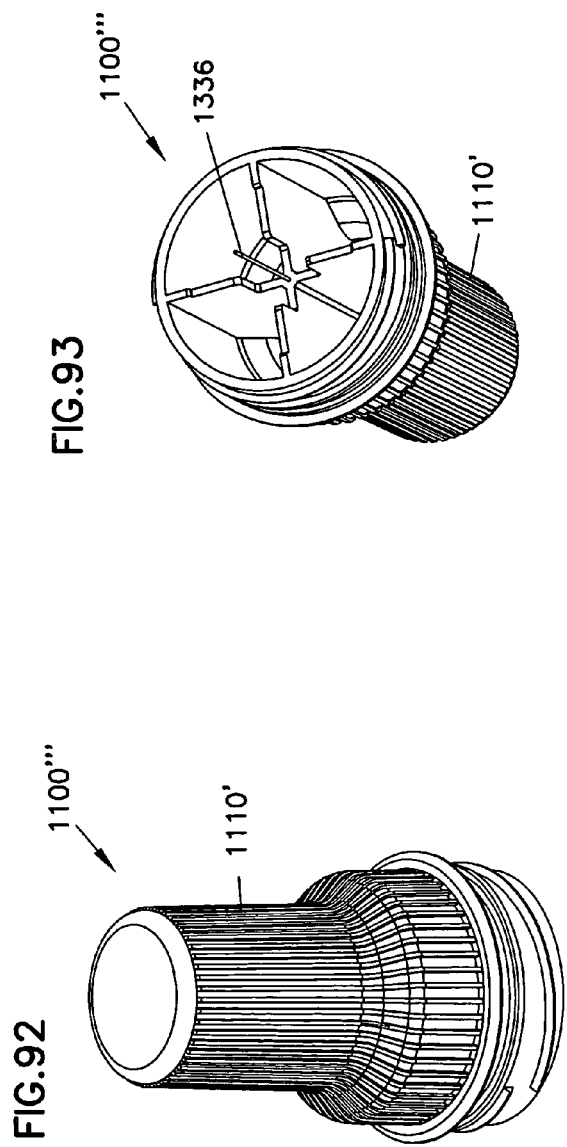

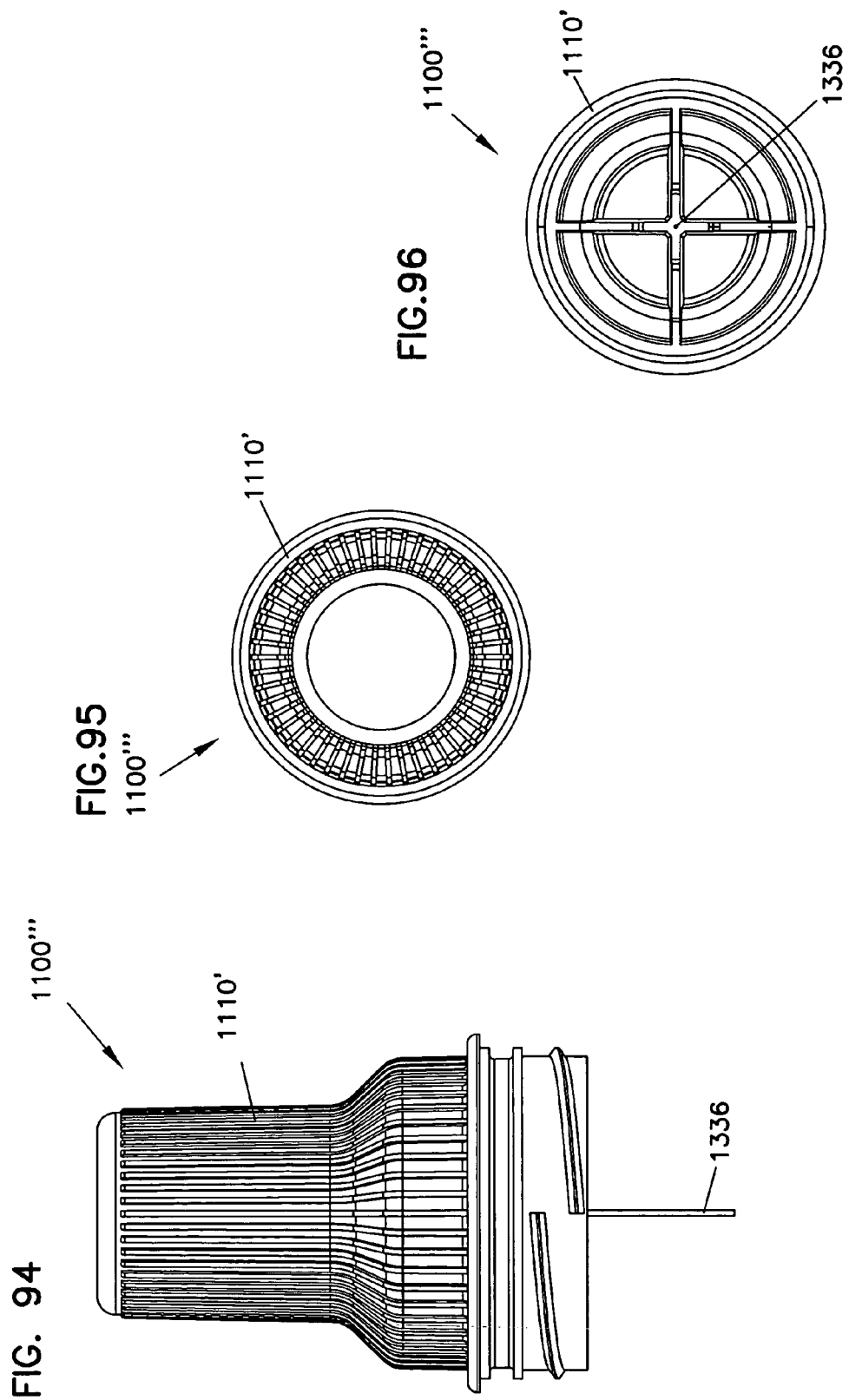

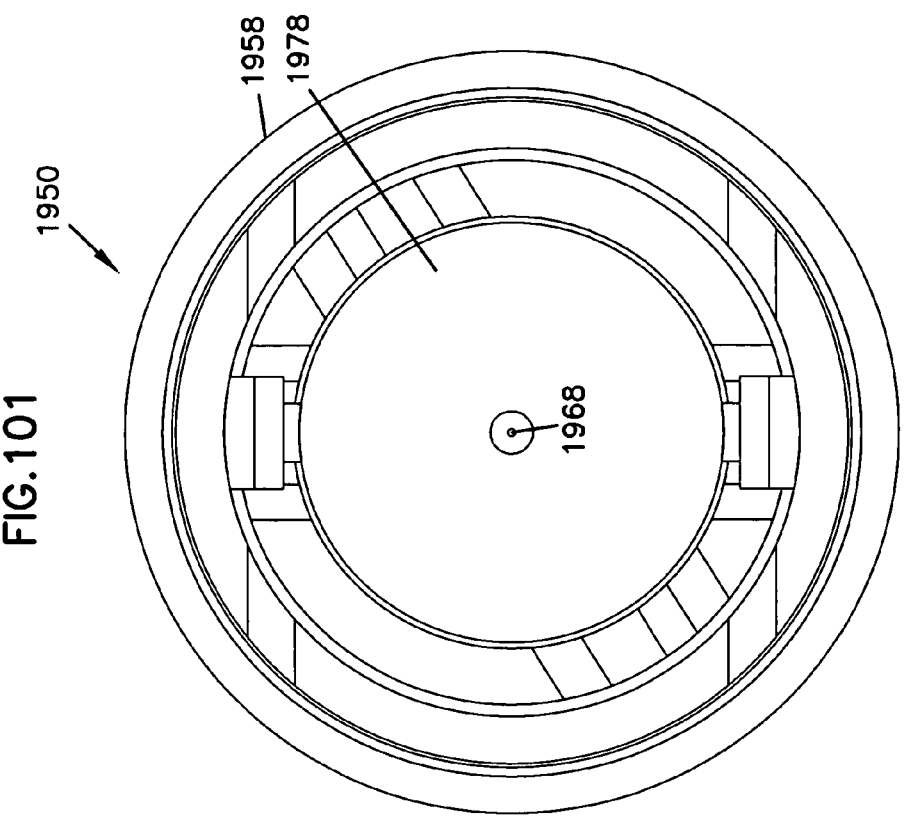
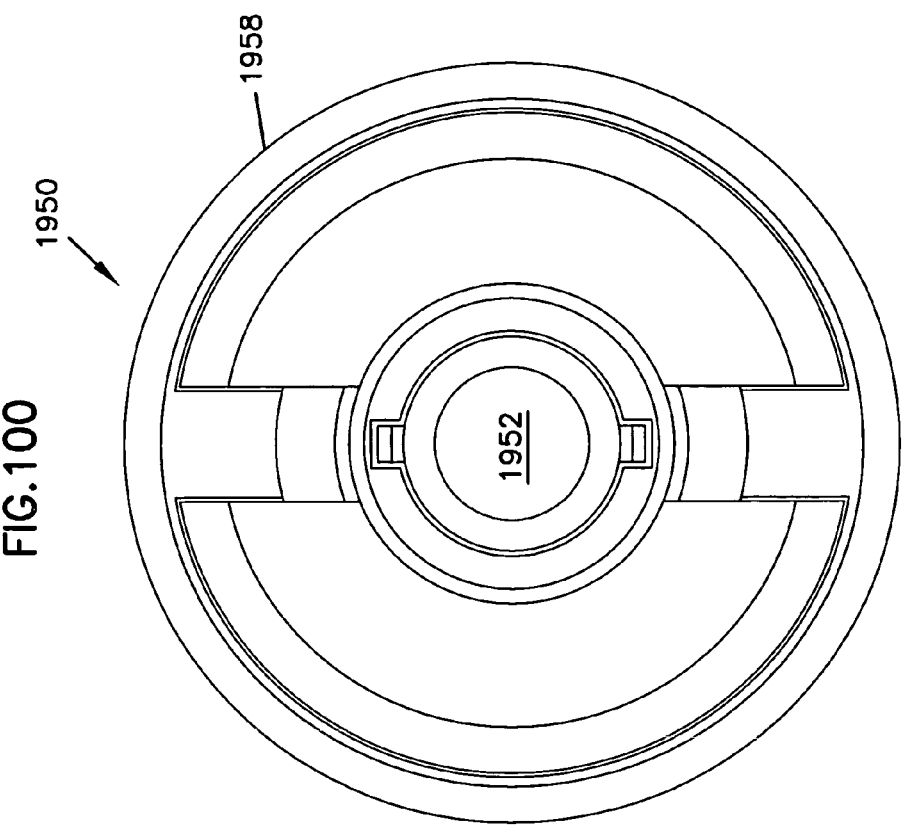

US 7,731,691 B2

SUBCUTANEOUS INFUSION DEVICE AND DEVICE FOR INSERTION OF A CANNULA OF AN INFUSION DEVICE AND METHOD

TECHNICAL FIELD

The present invention relates to an infusion device for delivery of a substance to a patient. The present invention also relates to a device for assisting in the introduction of a cannula of an infusion device into the skin of a patient.

BACKGROUND

Infusion devices are used to deliver substances such as medications into the subcutaneous layer of skin of a patient. Typically, an infusion device includes a cannula that is introduced into the skin, as well as a tube extending from the infusion device to, for example, an infusion pump to deliver the substance.

In current designs, it is typically necessary to introduce a cannula of the infusion device into the skin while maintaining the device at a given orientation so that the tubing extends in a direction towards the infusion pump. Further, once the infusion device is placed on the skin, there is typically no way to reorient the device and associated tubing, or to remove the tubing from the body without removing the cannula from the skin of the patient. In addition, the profile of infusion devices can be undesirably high, making placement and concealment of the infusion device difficult and uncomfortable to wear. Also, introduction of the infusion device into the skin can be complicated and require two hands to accomplish.

In addition, devices for assisting in insertion of the cannula of an infusion device into the skin of the patient are known. For example, some devices utilize springs to automatically drive a needle into the skin of a patient to introduce the cannula of the infusion device into the subcutaneous layer.

Because a needle is used to introduce the cannula of the infusion device into the subcutaneous layer of skin, there is a risk associated with inadvertent exposure to the needle. Further, patients may react adversely to viewing the needle prior to insertion and may, for example, be reluctant to place the needle into the skin. Prior devices may not adequately shroud this needle prior to and/or after introduction of the infusion device.

Other issues of concern in the design and use of insertion devices include ease of use by the patient and sterilization. For example, some patients may have difficulty loading the infusion device into the insertion device.

It is therefore desirable to provide new designs for infusion devices and devices used to assist in the introduction of an infusion device into the skin of a patient to deliver a substance into the skin.

SUMMARY

Embodiments made in accordance with the present invention are related to infusion devices for delivery of a substance to a patient. Embodiments made in accordance with the present invention also include devices that can be used to assist in the introduction of the cannula of an infusion device into the skin of a patient for delivery of a substance to the patient.

In one embodiment, an infusion device can include a site and a set. The site can include a cannula that is introduced into a subcutaneous layer of skin of the patient. The set can be coupled to the site by, for example, placing the set over the site and moving the set from an unlocked to a locked position. A substance can then be delivered through the set to the site and from the site into the patient through the cannula.

The set can preferably be oriented at multiple rotational orientations with respect to the site, and can preferably be coupled and uncoupled with the site multiple times.

In another embodiment, a device includes a needle used to insert the cannula of an infusion device into the skin of a patient. Once the cannula of the infusion device is inserted into the skin, the device moves the needle to a retracted state within the device.

In another embodiment, a device is configured to move a needle and associated cannula of an infusion device from a delivery state to a trigger state at which the cannula of the infusion device is inserted into the skin of a patient. Upon full insertion of the cannula at the trigger state, the device is then configured to move the needle to a retracted state within the device.

In another embodiment, a device includes a needle that can be used to insert a cannula of a site into the skin of a patient. Upon insertion of the cannula, the needle can be removed from the skin. In one embodiment, a cap is provided that can be placed onto the device prior to and after use of the device to provide a sterile environment and/or to reduce exposure to the needle.

In other embodiments, a subcutaneous infusion device and device for introduction of a cannula of the infusion device can be combined to introduce the cannula into the skin and deliver a substance into the skin.

The above summary of the present invention is not intended to describe each disclosed embodiment or every implementation of the present invention. Figures in the detailed description that follow more particularly exemplify embodiments of the invention. While certain embodiments will be illustrated and described, the invention is not limited to use in such embodiments.

DESCRIPTION OF THE DRAWINGS

FIG. 6 is a cross-sectional view taken along line 6-6 of the site of FIG. 3.

FIG. 6A is a cross-sectional view taken along line 6-6 of the site of FIG. 3 including a needle used to insert the site.

FIG. 21 is a top perspective view of an example embodiment of a set in an unlocked position made in accordance with the present invention.

FIG. 22 is a top perspective view of a first member of the set of FIG. 21.

FIG. 23 is a top view of the first member of FIG. 22.

FIG. 24 is a side view of the first member of FIG. 22.

FIG. 25 is an end view of the first member of FIG. 22.

FIG. 26 is another end view of the first member of FIG. 22.

FIG. 27 is a top perspective view of a second member of the set of FIG. 21.

FIG. 28 is a top view of the second member of FIG. 27.

FIG. 29 is a side view of the second member of FIG. 27.

FIG. 30 is an end view of the second member of FIG. 27.

FIG. 31 is another end view of the second member of FIG. 27.

FIG. 32 is a top view of the set of FIG. 21 in an unlocked position.

FIG. 33 is a side view of the set of FIG. 32.

FIG. 34 is an end view of the set of FIG. 32.

FIG. 39 is an end view of the set of FIG. 36.

FIG. 40 is a bottom perspective view of the set of FIG. 36.

FIG. 41 is a bottom view of the set of FIG. 36.

FIG. 42 is a cross-sectional view taken along line 42-42 of the set of FIG. 38 with portions of the set removed for clarity.

FIG. 56 is a perspective view of a housing of the device of FIG. 54.

FIG. 57 is a side view of the housing of FIG. 56.

FIG. 58 is an end view of the housing of FIG. 56.

FIG. 59 is a perspective view of a cylinder hub of the device of FIG. 54.

FIG. 60 is side view of the cylinder hub of FIG. 59.

FIG. 61 is another side view of the cylinder hub of FIG. 59.

FIG. 62 is an end view of the cylinder hub of FIG. 59.

FIG. 63 is a perspective view of a needle hub of the device of FIG. 54.

FIG. 64 is a side view of the needle hub of FIG. 63.

FIG. 65 is another side view of the needle hub of FIG. 63.

FIG. 66 is an end view of the needle hub of FIG. 63.

FIG. 67 is a perspective view of a sleeve of the device of FIG. 54.

FIG. 68 is a side view of the sleeve of FIG. 67.

FIG. 69 is another side view of the sleeve of FIG. 67.

FIG. 70 is an end view of the sleeve of FIG. 67.

FIG. 74 is a perspective view of a cap of the device of FIG. 54.

FIG. 75 is a side view of the cap of FIG. 74.

FIG. 76 is an end view of the cap of FIG. 74.

FIG. 77 is a side view of the device of FIG. 54 with the cap removed.

FIG. 78 is a side view of the device of FIG. 77 in a trigger state.

FIG. 80A is a cross-sectional view taken along line 80A-80A of the device of FIG. 77 in a delivery state.

FIG. 80B is a cross-sectional view taken along line 80B-80B of the device of FIG. 77 in the delivery state.

FIG. 81A is a cross-sectional view taken along line 81A-81A of the device of FIG. 78 in a trigger state.

FIG. 81B is a cross-sectional view taken along line 81B-81B of the device of FIG. 78 in the trigger state.

FIG. 81C is a cross-sectional view of the device of FIG. 81B illustrating the adhesive portion being sheared from a surface of the sleeve.

FIG. 83A is a cross-sectional view taken along line 83A-83A of the device of FIG. 77 in a retracted state.

FIG. 83B is a cross-sectional view taken along line 83B-83B of the device of FIG. 77 in the retracted state.

FIG. 84 is a cross-sectional view of a portion of another example embodiment of a device used to introduce an infusion device into a patient made in accordance with the present invention.

FIG. 87A is a cross-sectional view of the device of FIG. 85A in a retracted state.

FIG. 87B is a cross-sectional view of the device of FIG. 85B in the retracted state.

FIG. 88 is a perspective view of a sleeve of the device of FIG. 85A.

FIG. 89 is a side view of the sleeve of FIG. 88.

FIG. 90 is another side view of the sleeve of FIG. 88.

FIG. 91 is an end view of the sleeve of FIG. 88.

FIG. 92 is a perspective view of another example embodiment of a device used to introduce an infusion device into a patient made in accordance with the present invention.

FIG. 93 is another perspective view of the device of FIG. 92.

FIG. 94 is a side view of the device of FIG. 92.

FIG. 95 is an end view of the device of FIG. 92.

FIG. 96 is an opposite end view of the device of FIG. 92.

FIG. 100 is an end view of the device of FIG. 97.

FIG. 101 is another end view of the device of FIG. 97.

DETAILED DESCRIPTION

Figure 1:
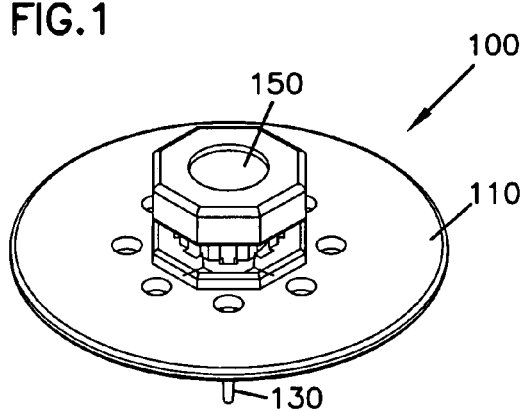
FIG. 1 is a top perspective view of an example embodiment of a site made in accordance with the present invention.
Figure 2:
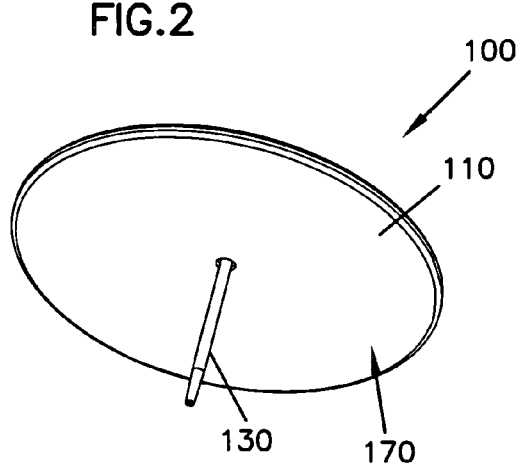
FIG. 2 is a bottom perspective view of the site of FIG. 1.
Figure 3:
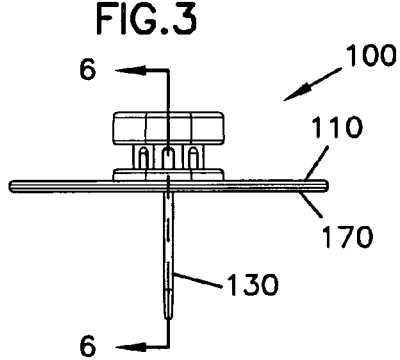
FIG. 3 is a side view of the site of FIG. 1.
Figure 4:
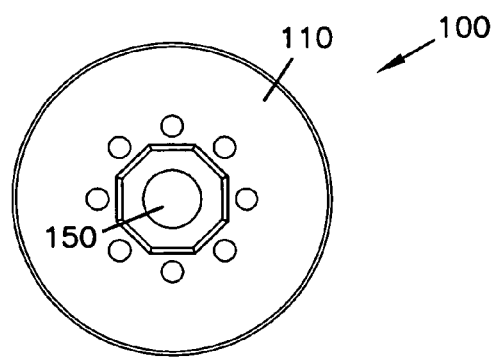
FIG. 4 is a top view of the site of FIG. 1.
Figure 5:
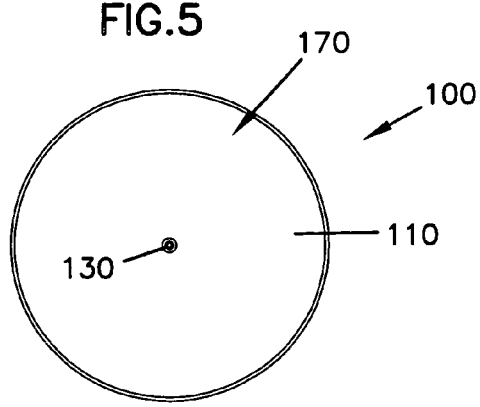
FIG. 5 is a bottom view of the site of FIG. 1.
Figure 7:
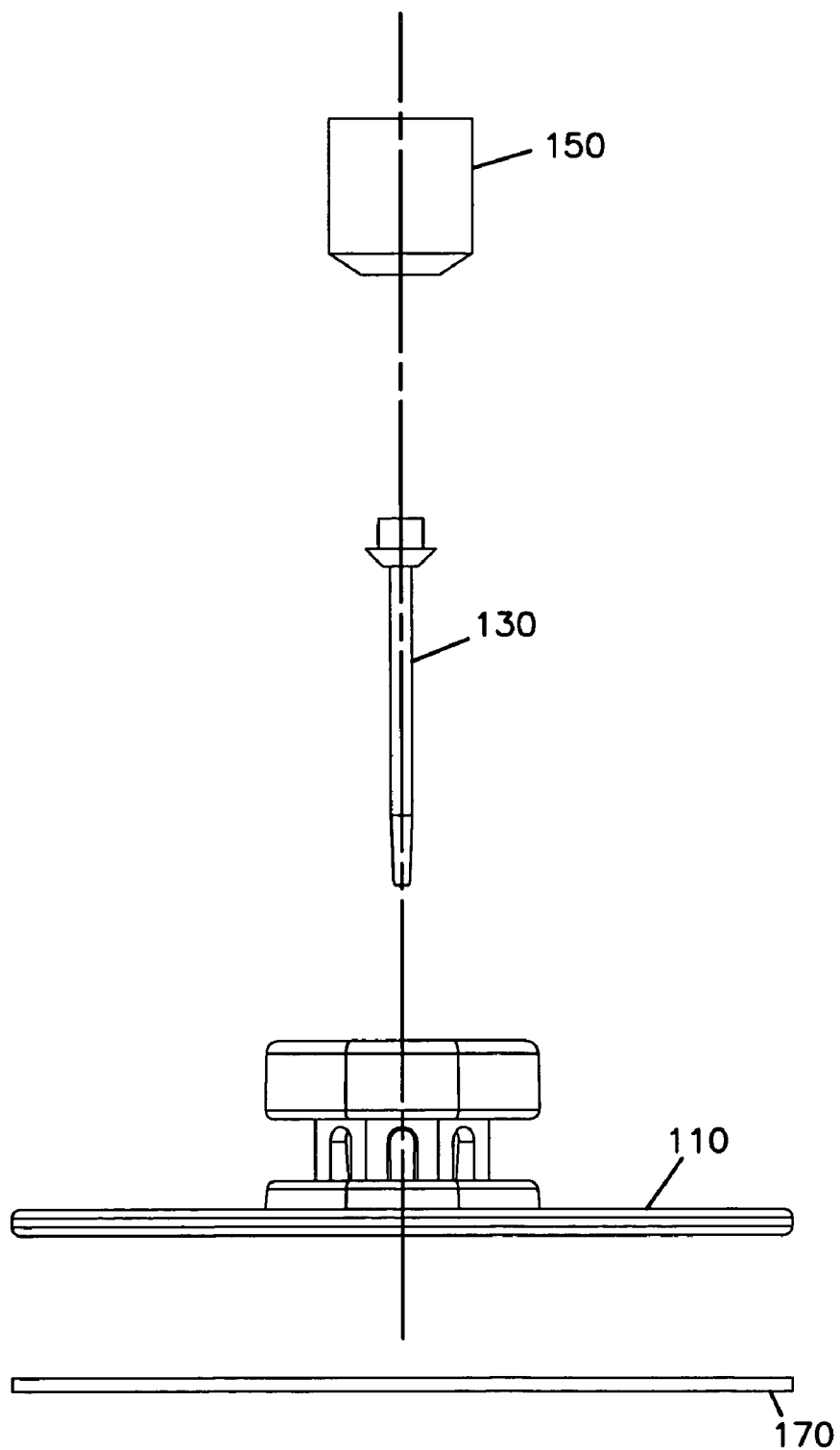
FIG. 7 is an exploded view of the site of FIG. 1.
Figure 8:
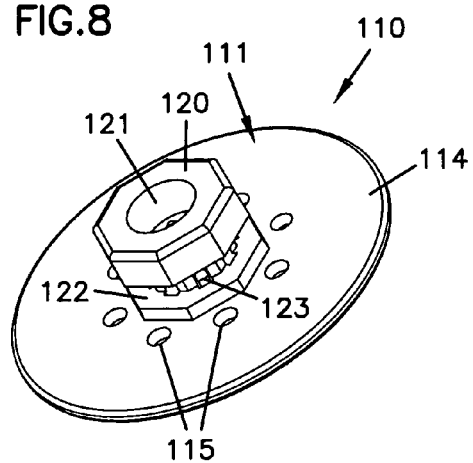
FIG. 8 is a top perspective view of a base of the site of FIG. 1.
Figure 9:
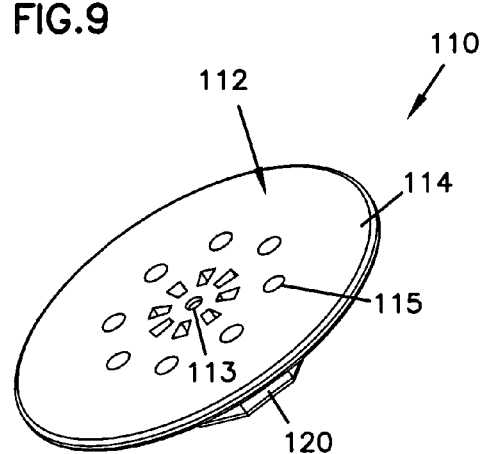
FIG. 9 is a bottom perspective view of the base of FIG. 8.
Figure 10:
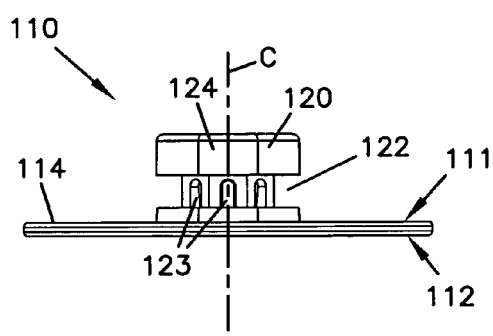
FIG. 10 is a side view of the base of FIG. 8.
Figure 11:
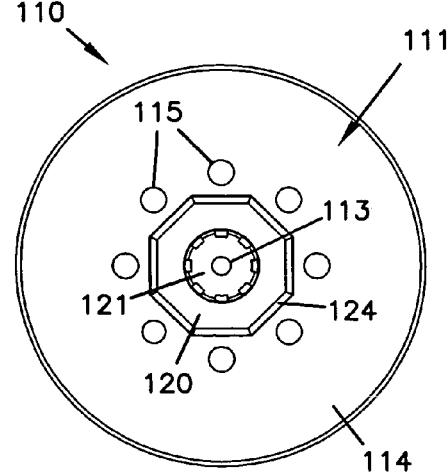
FIG. 11 is a top view of the base of FIG. 8.

Embodiments of the present invention relate to infusion devices for delivering a substance into the subcutaneous layer of skin of a patient. Embodiments of the present invention also relate to devices for assisting in the introduction of an infusion device, specifically a cannula of the infusion device, into the subcutaneous layer of skin of a patient.

Generally, the example infusion devices disclosed herein include a site with a cannula that is introduced into the subcutaneous layer of the skin of a patient to deliver a substance, as well as a set that can be coupled to the site to deliver the substance to the site.

Referring now to FIGS. 1-7, an example embodiment of a site 100 of an infusion device is depicted in accordance with the present invention. Generally, the site 100 can be used in conjunction with a set (described below) to deliver a substance into a patient.

The site 100 includes a base 110, a cannula 130, a diaphragm 150, and an adhesive portion 170. The cannula 130 of the site 100 can be introduced into the subcutaneous layer of skin of the patient using a needle (e.g., needle 139), as shown in FIG. 6A. The adhesive portion 170 allows the base 110 of the site 100 to be coupled to the skin of the patient. The diaphragm 150 is in fluid communication with the cannula to deliver a substance from the diaphragm 150, through the cannula 130, and into the skin of the patient, as described further below.

Referring now to FIGS. 8-11, the base 110 is shown. The base includes a stand 114 with a top side 111 and a bottom side 112, and forms a central aperture 113 located at a central axis C of the base 110. The stand 114 further forms eight positional slots 115 on the top side 111 positioned radially with respect to the central axis C of the site 110 at regular intervals.

The base 110 also includes a member 120 coupled to the stand 114, the member 120 being positioned about the central aperture 113 of the stand 114 and including eight surfaces 124. In one preferred embodiment, the member 120 is non-cylindrical in shape. For example, in the embodiment shown the member 120 is octagonal in shape, although other shapes can also be used, as noted below. The non-cylindrical shape of member 120 defines different mounting orientations for a set that can be coupled to the site 100.

An interior wall of the member 120 forms a cylindrical cavity 121, and an exterior periphery of the member 120 forms a groove 122 extending about the exterior periphery. In addition, the member 120 forms eight apertures 123 extending from the interior cavity 121 to the groove 122 in the exterior of the member 120.

Figure 12:
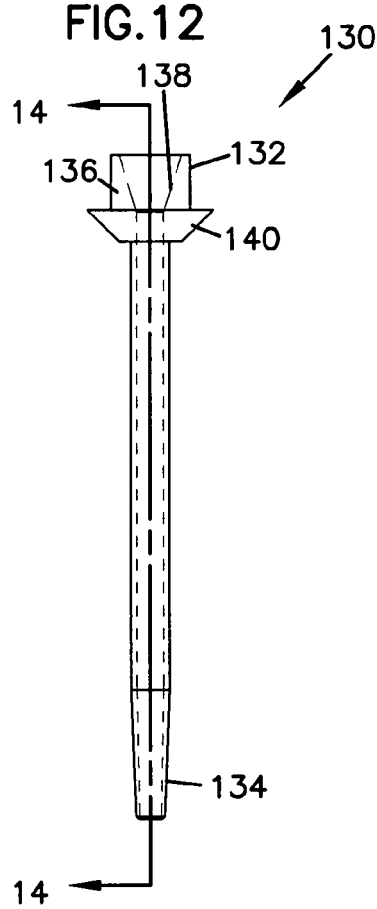
FIG. 12 is a side view of a cannula of the site of FIG. 1.
Figure 13:
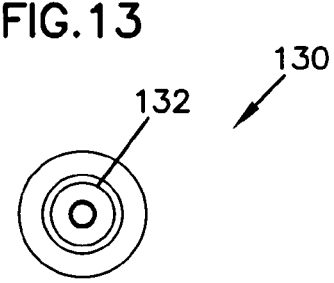
FIG. 13 is an end view of the cannula of FIG. 13.
Figure 14:
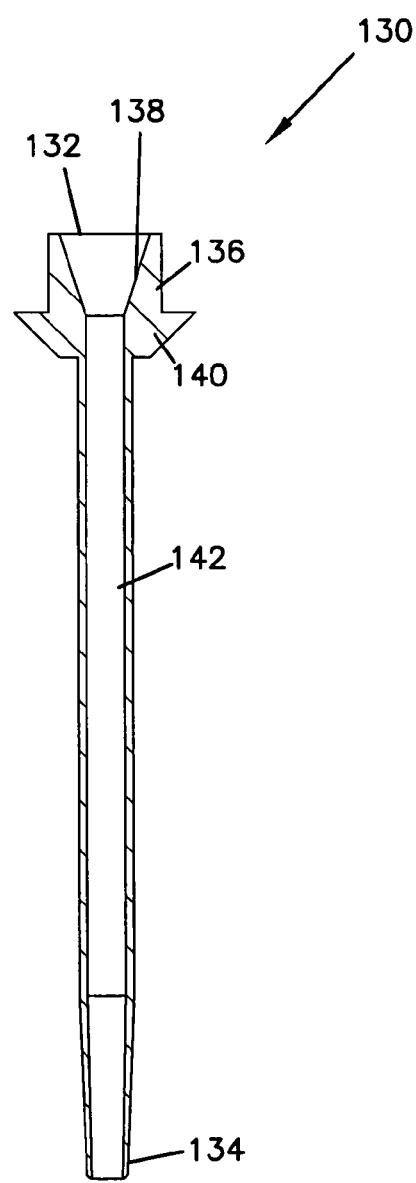
FIG. 14 is cross-sectional view taken along line 14-14 of the cannula of FIG. 12.

Referring now to FIGS. 12-14, the cannula 130 is illustrated. The cannula 130 includes first and second ends 132 and 134. The first end 132 of the cannula 130 includes a flange portion 136 having a tapered bottom side 140, as well as a tapered portion 138 described further below. The cannula 130 also includes a central bore 142 extending from the first end 132 to the second end 134 to allow a substance to be introduced at the first end 132 and delivered out of the second end 134.

The cannula 130 is positioned within the cavity 121 of the base 110 so that the bottom taper 140 of the cannula 130 engages tapered bottom surfaces 125 of the cavity 121 of the member 120, and the second end 134 of the cannula 130 extends through the central aperture 113 of the stand 114 at an approximate right angle to the bottom side 112 of the stand 114. See FIG. 6. Preferably, the bottom taper 140 of the cannula 130 is positioned adjacent to the stand 114 of the base 110.

Preferably the cannula 130 is made of fluorinated ethylene propylene (FEP). Other materials can also be used, such as polytetrafluoroethylene (PTFE), or other suitable plastics.

Figure 15:
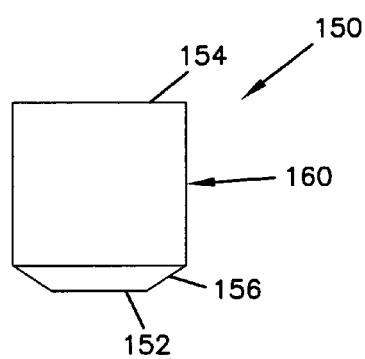
FIG. 15 is a side view of a diaphragm of the site of FIG. 1.
Figure 16:
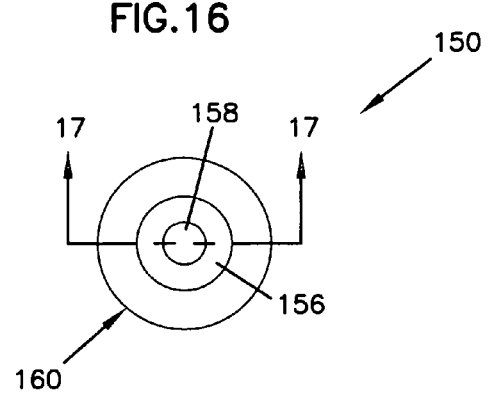
FIG. 16 is an end view of the diaphragm of FIG. 15.
Figure 17:
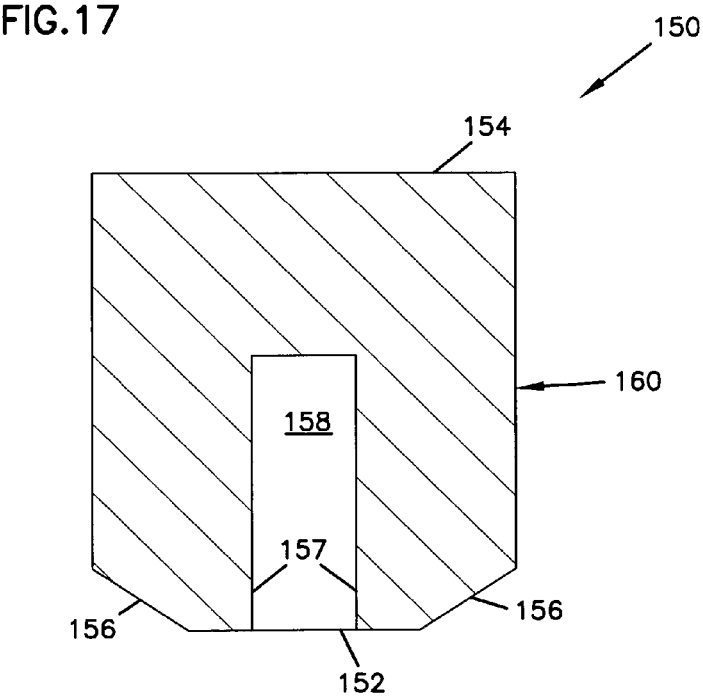
FIG. 17 is a cross-sectional view taken along line 17-17 of the diaphragm of FIG. 16.

Referring now to FIGS. 15-17, the diaphragm 150 is shown. Generally, the diaphragm 150 functions as a septum or seal that allows a needle to access an internal portion of the septum to deliver a substance provided, for example, from an infusion device or other similar device to the cannula 130.

Preferably, the diaphragm 150 is generally cylindrical in shape and includes an open bottom end 152 and a closed top end 154. The diaphragm 150 also includes a tapered portion 156 adjacent the bottom end 152, and a central reservoir 158.

As shown, for example, in FIGS. 6 and 17, the diaphragm 150 is positioned in the cavity 121 of the member 120 and preferably includes an outer periphery 160 that is sized to frictionally engage the interior cavity wall of the member 120 to retain the diaphragm 150 in the cavity 121. In addition, the tapered portion 156 of the diaphragm 150 is configured to engage the tapered bottom surfaces 125 of the base 110. The bottom end 152 engages the first end 132 of the cannula 130 to provide fluid communication between the reservoir 158 and the bore 142 of the cannula 130.

More specifically, surfaces 157 adjacent to the bottom end 152 of diaphragm 150 preferably are compressed against the first end 132 of the cannula 130 to provide a seal with respect to the cannula 130 so a substance can be delivered from the diaphragm 150, through the cannula 130, and into the patient. In alternative embodiments, additional structure such as, for example, an O-ring can also be provided between the diaphragm 150 and cannula 130 to provide additional sealing.

In a preferred embodiment, the diaphragm 150 is made of a silicone elastomer. Other materials can also be used, such as ethylene propylene or other suitable elastomeric materials.

As previously noted, preferably the diaphragm 150 is retained in the cavity 121 of the member 120 of the base 110 through the frictional engagement of the outer periphery 160 of the diaphragm 150 with the walls of the cavity 121. In alternative embodiments, a retaining member can be fitted over the open top of the member 120 to further retain the diaphragm 150 in position in the cavity 121. In other embodiments, the diaphragm 150 can be retained in the cavity 121 through compression by other features of the member 120, or the diaphragm 150 can have features that mate with features of the member 120. For example, in one alternative embodiment, the diaphragm 150 can be formed with barbs on the outer periphery 160 positioned and sized to be received within apertures 123 formed in the member 120 to retain the diaphragm 150 in the cavity 120. Other configurations are also possible.

Figure 18:
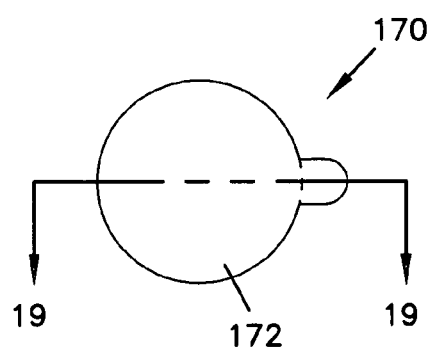
FIG. 18 is a top view of an adhesive portion of the site of FIG. 1.
Figure 19:
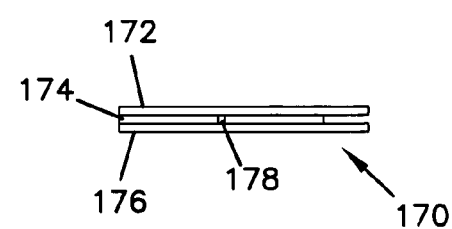
FIG. 19 is a cross-sectional view taken along line 19-19 of the adhesive portion of FIG. 18.
Figure 20:
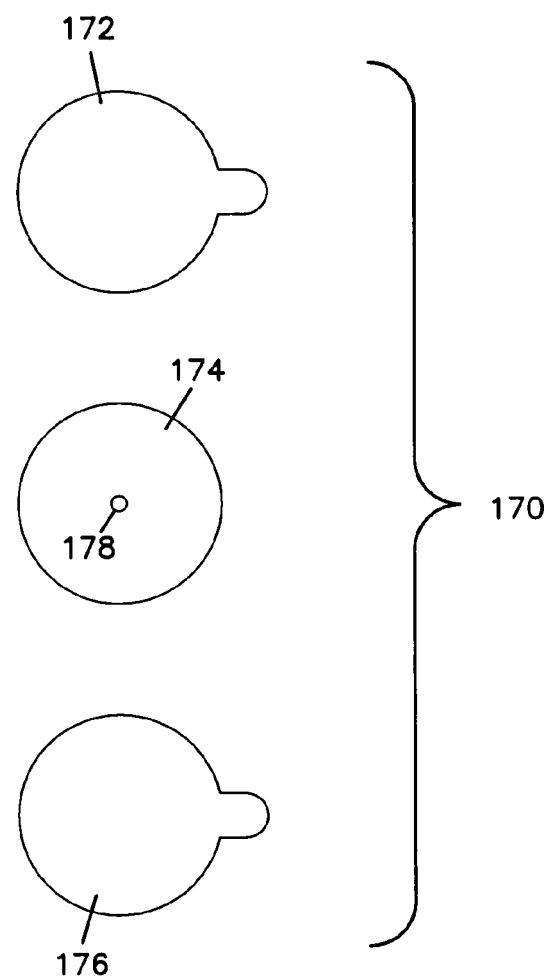
FIG. 20 is an exploded view of the adhesive portion of FIG. 18.

Referring now to FIGS. 18-20, the adhesive portion 170 is shown. The adhesive portion includes liners 172 and 176 sandwiching a layer 174. Preferably, the layer 174 includes an aperture 178 through which the cannula 130 of the site 100 extends, as described below.

The liner 172 can be removed and the layer 174 coupled to the bottom side 112 of the stand 114 of the base 110 using an adhesive. Examples of such adhesives include, without limitation, acrylic adhesive, synthetic rubber-based adhesive, acrylate adhesive, and silicone-based adhesive. In addition, the liner 176 can be removed and an adhesive be provided on a bottom side of the layer 174 to couple the adhesive portion 170 and associated site 100 to another adhesive portion or the skin of the patient, for example.

In a preferred embodiment, layer 174 of the adhesive portion 170 includes films with adhesives thereon, such as and without limitation, 3M™ 1577 tape. Other materials can also be used.

In other alternative embodiments, the adhesive portion 170 can be removed completely, and adhesion between the site 100 and skin of the patient can be provided using film and/or adhesive carried on other structures, such as a device used to insert the site 100 into the body, as described further below. Or, the layer 174 can be replaced or supplemented by one or more layers of other material such as, for example, a Tegaderm™ film manufactured by 3M™ or an IV3000™ film manufactured by Smith & Nephew.

In an alternative embodiment, layer 174 can be provided with a tab (not shown, but preferably similar to tabs shown on liners 172 and 176) or other similar structure that can assist the patient in removing the layer 174 and associated site 100 from the skin when desired. For example, the tab can extend from an outer periphery of the layer 174 and allow the patient to grasp the tab and thereby peel the layer 174 from the skin to remove the site 100.

In another alternative embodiment, the layer 174 can include a foam backing or similar additional material can be added adjacent to the layer 174 to provide supplemental cushioning as the site 100 is inserted into the skin of the patient.

Referring now to FIG. 21, an example embodiment of a set 200 of an infusion device is depicted in accordance with the present invention. As noted generally above and described further below, the set 200 can be used in conjunction with a site (e.g., site 100) to deliver a substance into a patient.

The set 200 generally includes a first member 210 and a second member 250. The first member 210 is slideable relative to the second member 250 into an unlocked position (see, e.g., FIGS. 21 and 32-35) and a locked position (see, e.g., FIGS. 36-42), described further below.

Referring now to FIGS. 22-26, the first member 210 is shown. The first member 210 includes a main body 212, and a port 213 extending through the body 212 and in fluid communication with a hollow needle 214. The port 213 is preferably coupled to a tube (e.g., tube 305 shown in FIG. 21) that can be attached, for example, to an infusion pump for the delivery of a substance to the set 200.

The first member 210 also includes outer arms 220 and 222 with barbs 223 formed on the ends and projections 230 extending below the arms 220. In addition, the first member 210 includes inner arms 226 and 228 with barbs 229. As described further below, the outer arms 220 and 222 can be displaced towards one another when force is applied to surfaces 221.

Referring now to FIGS. 27-31, the second member 250 is shown. The second member 250 includes a main body 260, and a central octagonal aperture 270. The second member 250 also includes opening 262 extending to the central aperture 270, as well as openings 264 positioned on opposite sides of the main body 260. The second member 250 also includes projections 266 formed on a bottom surface 274 of a base 261, as well as slots 268 preferably extending through the base 261 of the main body 260.

Referring now to FIGS. 21 and 32-35, the first and second members 210 and 250 of the set 200 are shown in the unlocked position. The first member 210 is slidingly received by the second member 250 such that inner arms 226 and 228 are accepted into opening 262 of the second member 250. Projections 230 on outer arms 220 and 222 of the first member 210 are received in slots 268 of the second member 250.

Figure 35:
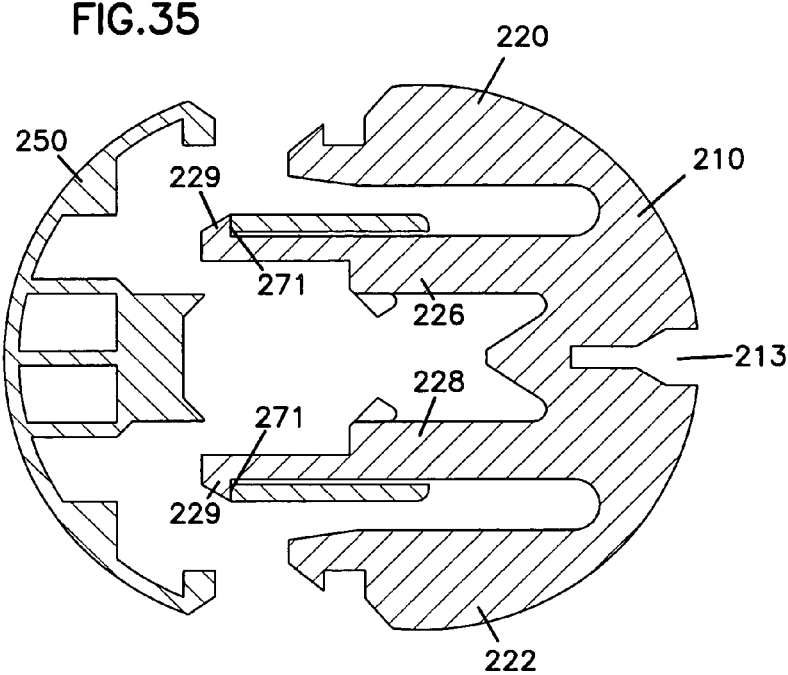
FIG. 35 is a cross-sectional view taken along line 35-35 of the set of FIG. 32 with portions of the set removed for clarity.
Figure 36:
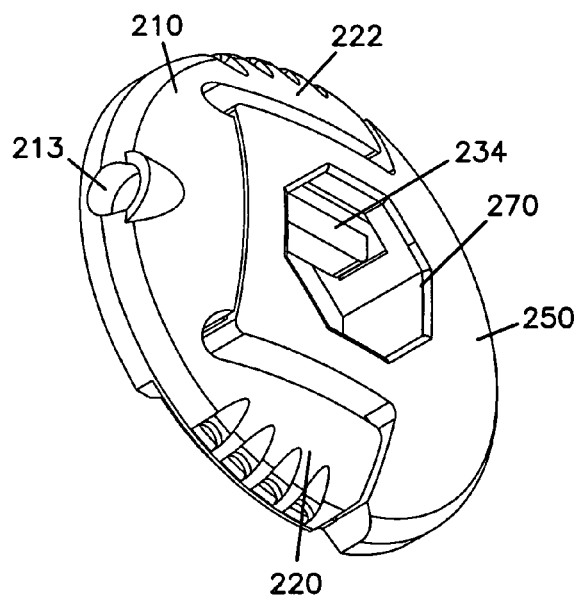
FIG. 36 is a top perspective view of the set of FIG. 21 in a locked position.
Figure 37:
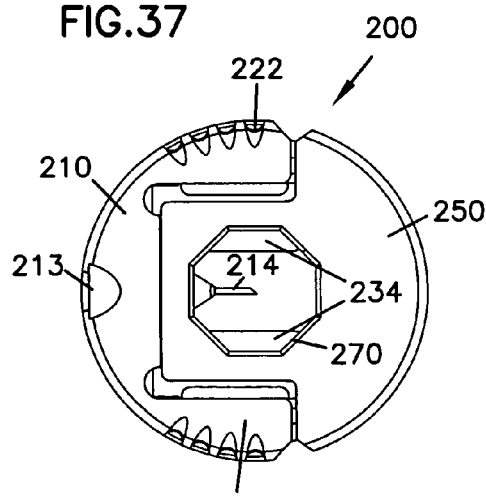
FIG. 37 is a top view of the set of FIG. 36.
Figure 38:
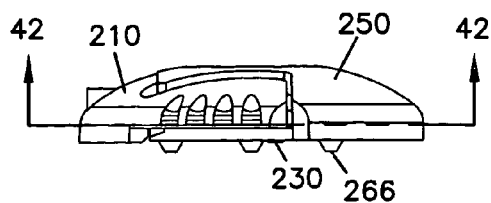
FIG. 38 is a side view of the set of FIG. 36.
Figure 43:
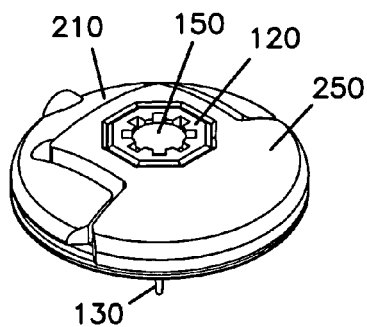
FIG. 43 is a perspective view of the site of FIG. 1 and the set of FIG. 21 coupled to one another.
Figure 44:
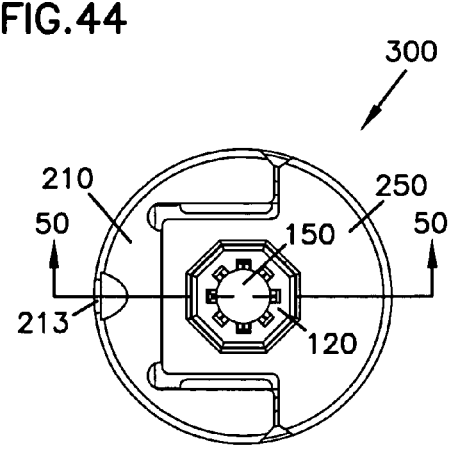
FIG. 44 is a top view of the site and set of FIG. 43.
Figure 45:
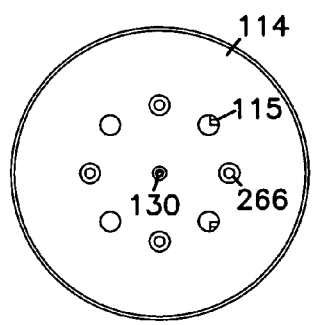
FIG. 45 is a bottom view of the site and set of FIG. 43.
Figure 46:
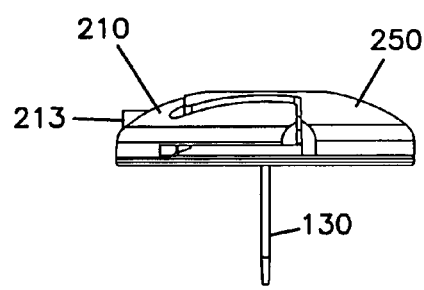
FIG. 46 is a side view of the site and set of FIG. 43.
Figure 47:
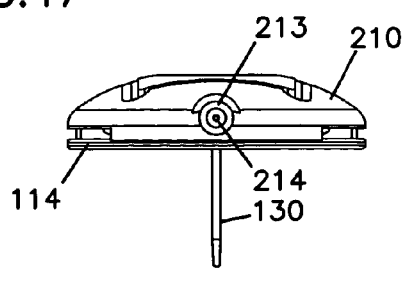
FIG. 47 is an end view of the site and set of FIG. 43.
Figure 48:
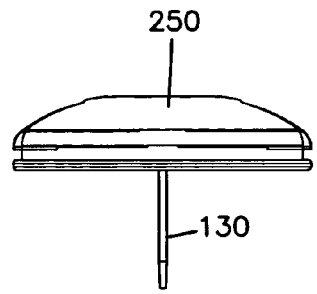
FIG. 48 is another end view of the site and set of FIG. 43.
Figure 49:
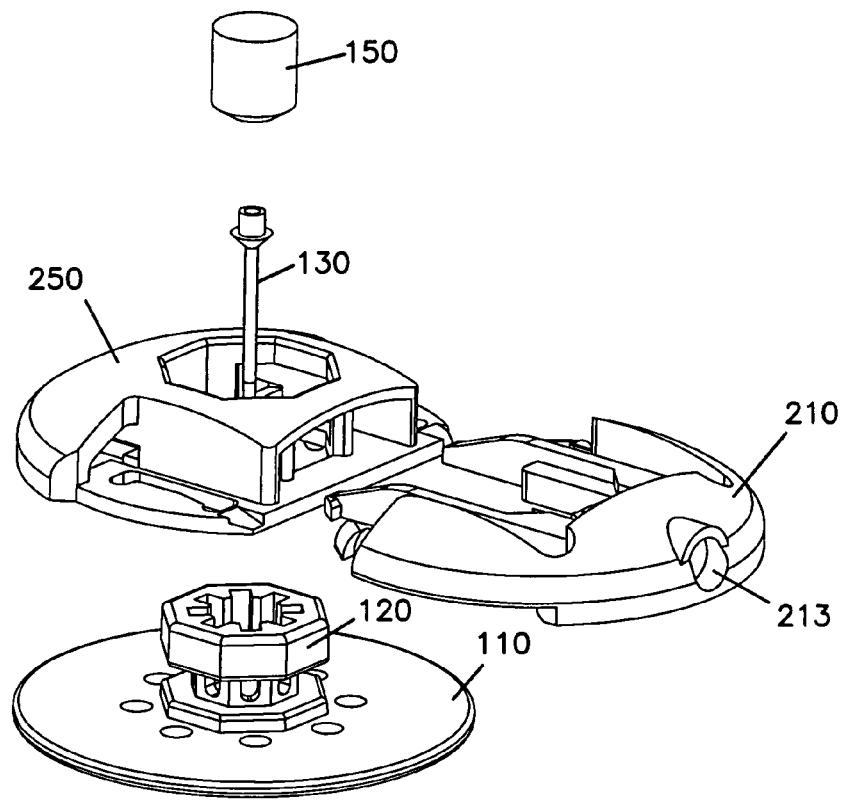
FIG. 49 is an exploded perspective view of the site and set of FIG. 43.

As illustrated by FIG. 35, in the unlocked position barbs 229 of inner arms 226 and 228 of the first member 210 extend through openings 264 and engage shoulders 271 of the second member 250 such that the first and second members 210 and 250 cannot be further separated.

Referring now to FIGS. 36-42, the first and second members 210 and 250 of the set 200 are shown in the locked position. To move the set 200 from the unlocked to the locked position, the first and second members 210 and 250 are slid towards one another, and outer arms 220 and 222 of the first member 210 are accepted into the openings 264 of the second member 250. Likewise, projections 230 on outer arms 220 and 222 slide along slots 268 of the second member 250. Further, surfaces 234 of the inner arms 226 and 228 partially extend into aperture 270, as described further below.

As illustrated by FIG. 42, in the locked position outer arms 220 and 222 extend through openings 264 and engage lips 272 of the second member 250. In addition, inner arms 226 and 228 of the first member 210 extend further into the second member 250. In this locked position, the engagement of the barbs 223 with the lips 272 resist allowing the first member 210 from being slid relative to the second member 250.

In order to slide the first member 210 away from the second member 250 from the locked position back to the unlocked position, the outer arms 220 and 222 are deflected inwardly toward one another by applying pressure on surfaces 221 until the barbs 223 clear the lips 272, thereby allowing the first member 210 to be slid with respect to the second member 250 back into the unlocked position as shown in FIGS. 21 and 32-35.

Preferably, slots 268 formed in the second member 250 include a cammed surface 269 so that projections 230 extending below the arms 220 of the first member 210 are biased towards a first end 267 of the slots 268 to thereby bias the first member 210 into the unlocked position. See FIGS. 40 and 41. In alternative embodiments, other features can be provided to bias the first member 210 into the unlocked position. For example, detents can be provided to engage barbs 229 as inner arms 226 and 228 of the first member 210 are moved towards the locked position to bias the first member 210 into the unlocked position. It can be preferable to bias the set 200 into the unlocked position so that the set 200 can be easily positioned onto and removed from the site 100, as described further below.

Referring now to FIGS. 43-50, as previously noted the site 100 and set 200 can be used together to form an infusion device 300 for delivery of a substance to a patient.

One method of use of the infusion device 300 is as follows. Initially, the site 100 is positioned on the skin of a patient with the cannula 130 being introduced into the subcutaneous layer of the skin. This can be accomplished, for example, using a needle (e.g., needle 130 shown in FIG. 6A) that is extended through the exposed closed end 154 of the diaphragm 150 and through the bore 142 of the cannula 130 and beyond the second end 134. The tapered portion 138 of the flange portion 136 of the cannula 130 can assist in directing the needle through into the bore 142 of the cannula 130. In this position, the needle can be used to introduce the cannula 130 of the site 100 into the skin of the-patient. Further, once the cannula 130 is in position, the needle can be removed, leaving the cannula 130 in place in the subcutaneous layer of the skin. As the needle is removed, the closed end 154 of the diaphragm 150 reseals itself to retain the fluid-tight reservoir 158.

In a preferred embodiment, the site 100 of the infusion device 300 is placed in position on the skin of a patient using one or more of the devices or methods described below with reference to FIGS. 54-105.

Once the site 100 has been positioned on the skin of a patient (with the cannula 130 having been introduced into the subcutaneous layer), the set 200 can be coupled to the site 100 as follows. With the set 200 in the unlocked position, the set 200 can be placed over the member 120 so that the central octagonal aperture 270 of the set 200 accepts the member 120 into the aperture 270. The set 200 is lowered onto the site 100 until the bottom surface 274 of the set 200 contacts the stand 114 of the site 100 and projections 266 of the second member 250 are accepted into the positional slots 115 of the stand 114 of the base 110.

In this position on the site 100, the first member 210 of the set 200 can be slid from the unlocked to the locked position. As the first member 210 is slid to the locked position, surfaces 234 of the inner arms 226 and 228 (see FIGS. 23, 36, and 37) are accepted by the groove 112 of the member 120 of the base 100, which locks the set 200 to the site 100 so that the set 200 resists any upward force tending to remove the set 200 from the site 100 when the set 200 is in the locked position. In addition, the shape of the member 120 of the site 100 and the central aperture 270 of the set 200, as well as projections 266 received in slots 115, orient the set 200 with respect to the site 100 and function to resist rotation of the set 200 with respect to the site 100 when the set 200 is in the locked position.

Figure 50:
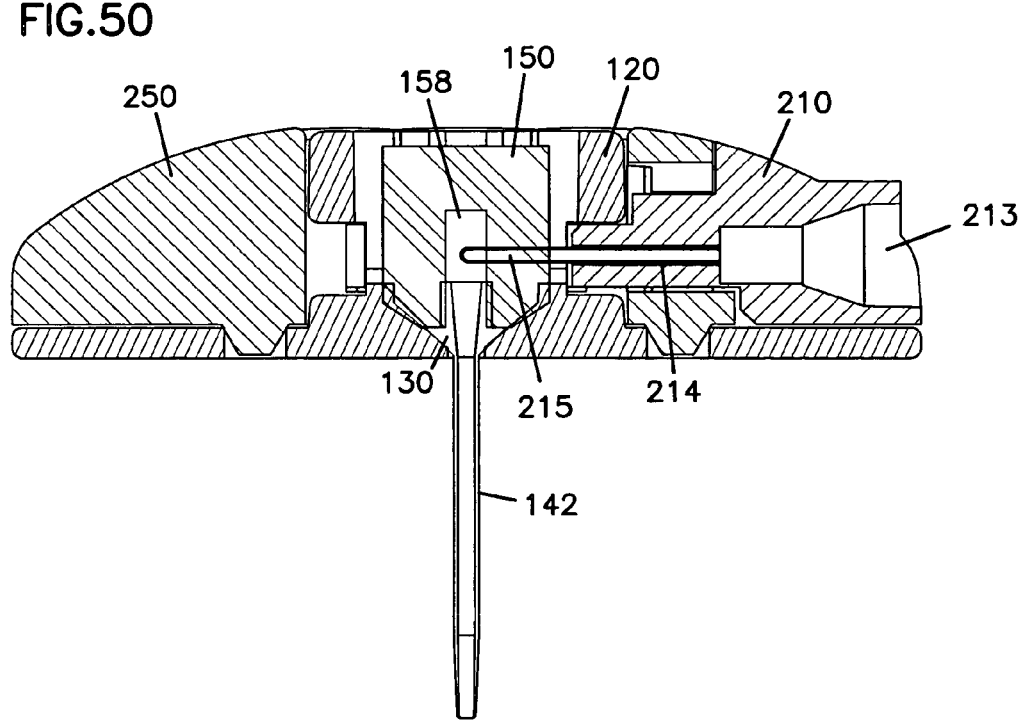
FIG. 50 is a cross-sectional view taken along line 50-50 of the site and set of FIG. 44.

In addition, as the first member 210 of the set 200 is moved from the unlocked to the locked position, the needle 214 is advanced through one of the eight apertures 123 formed in the member 120 and into the diaphragm 150 in the cavity 121. In the fully locked position as shown in FIG. 50, an end 215 of the needle 214 is positioned within the reservoir 158 of the diaphragm 150. In this position, the port 213 is fluidly coupled to the cavity 121 of the diaphragm 150 through the hollow needle 214, and the cavity 121 is in turn fluidly coupled to the skin of the patient through the bore 142 in the cannula 130. In this manner, a substance can be delivered to the port 213 of the set 200 (by, for example, a tube not shown in the figures), through the needle 214, into the reservoir 158, and into the subcutaneous layer of the skin of the patient by the cannula 130.

If the set 200 is not oriented as desired with respect to the site 100, or if the patient desires to remove the set 200 from the site 100, the set 200 can be moved from the locked to the unlocked position by forcing the outer arms 220 and 222 together and sliding the first member 210 away from the second member 250 to the unlocked position. This action removes the surfaces 234 from the groove 122, as well as the needle 214 from the reservoir 158. The diaphragm 150 reseals upon removal of the needle 214. The set 200 can then be removed from the site 100, leaving the site 100 in place on the skin of the patient. The set 200 can be replaced at another orientation or at a later time.

In the illustrated embodiment of the infusion device 300, the set 200 can be oriented and fixed in eight different positions with respect to the site 100. In alternative embodiments, the site 100 and set 200 can be configured to include fewer or more positions as desired. For example, in an alternative embodiment the member 120 of the site 100 and the aperture 270 of the set 200 can be formed in the shape of a square if four orientational positions are desired.

Figure 52:
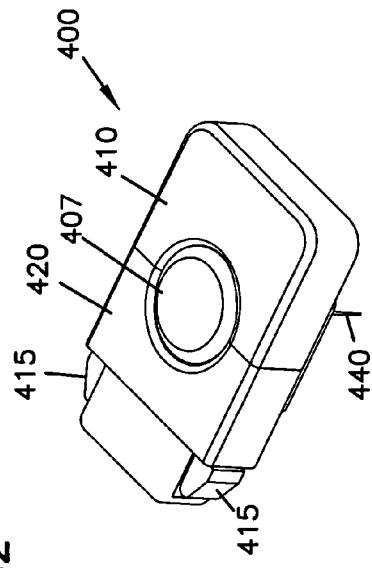
FIG. 52 is a perspective view of the infusion device of FIG. 51 in a locked position.
Figure 53:
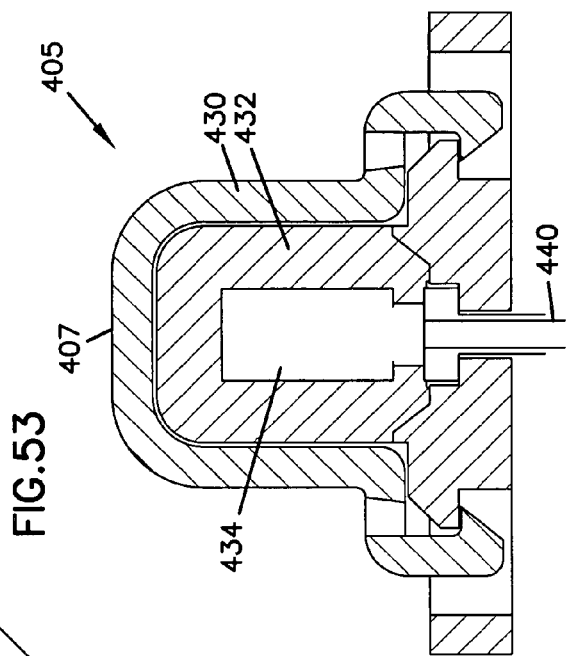
FIG. 53 is a cross-sectional view of the site of FIG. 51.
Figure 51:
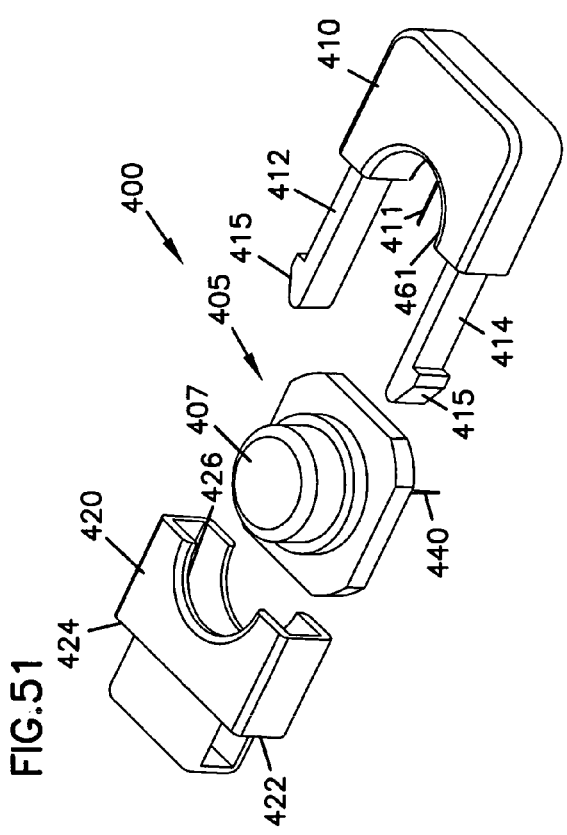
FIG. 51 is an exploded perspective view of another example embodiment of an infusion device including a site and set made in accordance with the present invention.

Referring now to FIGS. 51-53, another example infusion device 400 is shown in accordance with the present invention. The device 400 is similar to the example device 300 described above, except for the details noted below.

The infusion device 400 includes a site 405 with a central portion 407. The central portion 407 includes a pierceable outer shell 430 made of a material such as a plastic, and a softer inner diaphragm 432 surrounding the outer shell 430. An inner reservoir 434 of the central portion 407 is fluidly coupled to a cannula 440. See FIG. 53.

The infusion device 400 also includes a set with a first member 410 and a second member 420. The first member 410 includes a needle 411, and first and second arms 412 and 414 with barbs 415 on ends. The second member 420 includes shoulders 422 and 424. The first and second members 410 and 420 each form openings 461 and 426, respectively, that are sized to each receive a portion of the central portion 407 of the site 405.

The infusion device 400 can be used as follows. First, the site 405 is positioned on the skin of a patient so that the cannula 440 is introduced into the subcutaneous layer. Next, the first member 410 and second member 420 of the site are placed onto the site 405 so that openings 461 and 426 are positioned about the central portion 407, and the first and second members 410 and 420 are slid towards one another from the unlocked to the locked position. As the set is moved to the locked position, the needle 411 is introduced into the central portion 407 of the site 405, moving through the outer shell 430 and into the reservoir 434 to become fluidly coupled to the cannula 440. In addition, the arms 412 and 414 are accepted into the second member 420 until barbs 415 engage the shoulders 422 and 424 in the locked position, as shown in FIG. 52.

To move the set from the locked position back into the unlocked position, the barbs 415 are pressed inwardly toward one another until they clear the shoulders 422 and 424, and then the first member 410 is slid away from the second member 420, thereby removing the needle 411 from the central portion 407 of the site 405.

As preferably there is no specific structure provided with infusion device 400 for rotationally orienting the set with the site 405, the set can be oriented at an infinite number of rotational positions with respect to the site 405 as desired. Further, since the central portion 407 of the site and the openings 461 and 426 of the set are preferably circular in shape, the first and second members 410 and 420 of the site can be rotated relative to the site 405 without requiring that the set be completely removed from the site 405.

Figure 54:
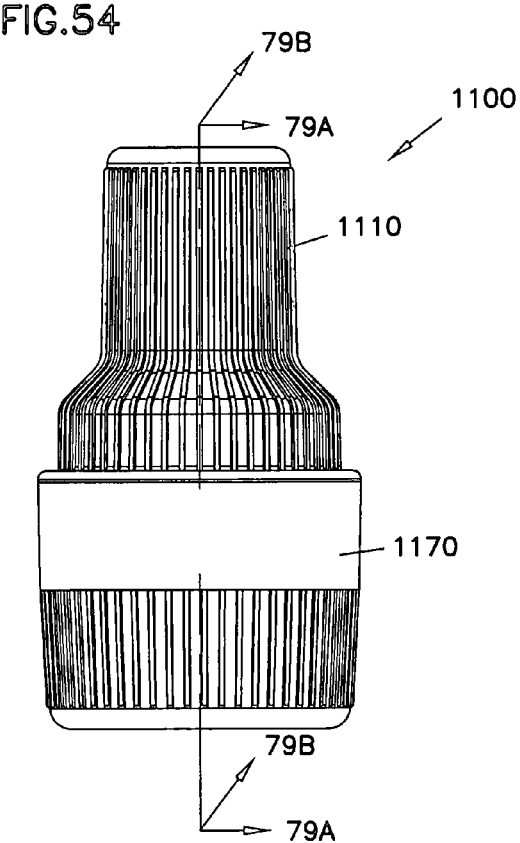
FIG. 54 is a side view of an example embodiment of a device used to introduce a cannula of an infusion device into a patient made in accordance with the present invention.
Figure 105:
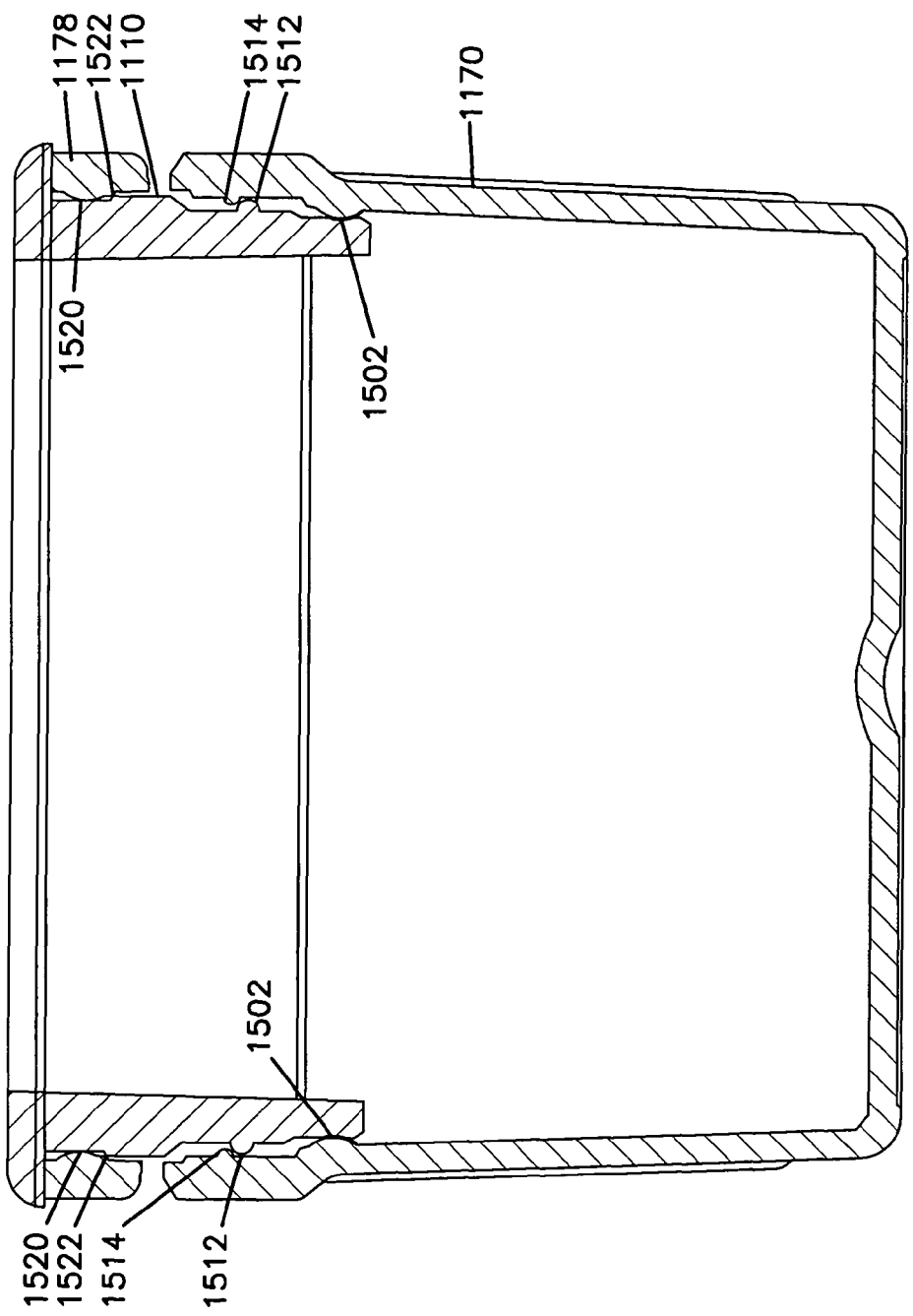
FIG. 105 is a cross-sectional view taken along line 105-105 of a portion of the device of FIG. 103.

Referring now to FIGS. 54-105, example devices and methods for placing a subcutaneous infusion device, such as site 100, into a subcutaneous layer of skin of a patient are disclosed.

Figure 55:
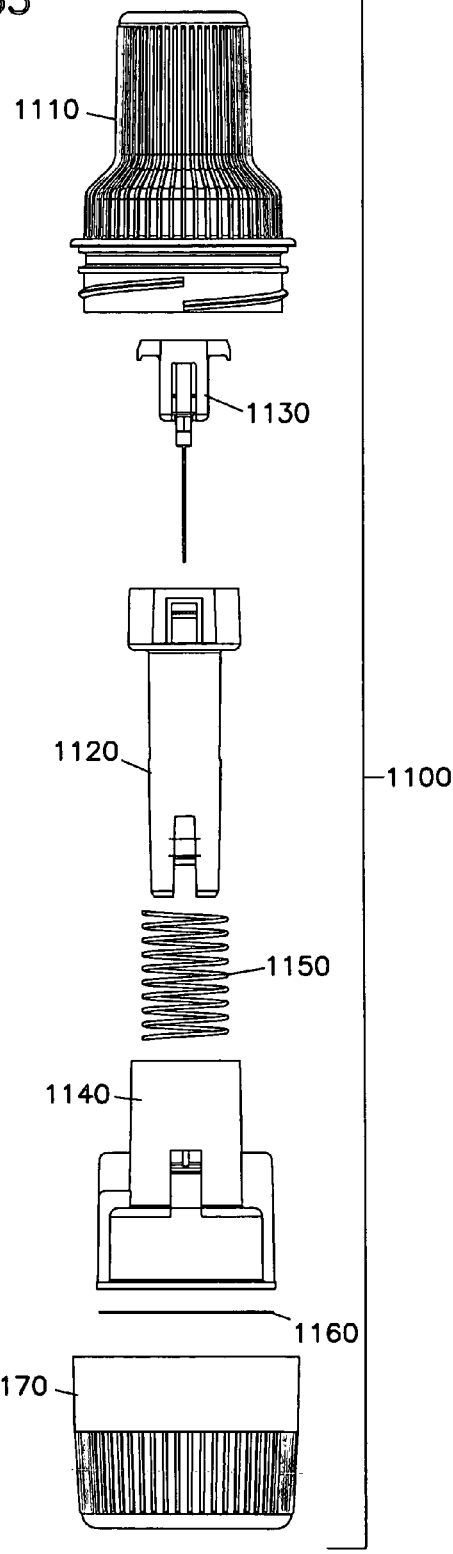
FIG. 55 is an exploded side view of the device of FIG. 54.

Referring to FIGS. 54 and 55, one example embodiment of a device 1100 is shown. The device 1100 is used to introduce a cannula of an infusion device, such as a set, site, or other access device, into the skin of the patient. The set, site, or other access device can then be used to deliver drugs or other fluid to the patient, such as from an infusion pump.

The device 1100 generally includes a housing 1110, a cylinder hub 1120, a needle hub 1130, a sleeve 1140, a spring 1150, an adhesive portion 1160, and a cap 1170. Each of the components of the device 1100, described further below, is configured to assist in the introduction of a cannula of an infusion device into the skin of a patient.

Referring now to FIGS. 56-58, the housing 1110 is shown. The housing 1110 is preferably cylindrical in shape and includes a closed upper end 1111 and an open lower end 1112. The housing 1110 further preferably includes a portion 1118 with a knurled surface to enhance a patient's grip on the housing 1110, as well as a threaded portion 1113 positioned adjacent the open lower end 1112.

Referring now to FIGS. 59-62, the cylinder hub 1120 is shown in greater detail. The cylinder hub 1120 includes first and second ends 1221 and 1222 and an interior passage 1223. In addition, two opposing slots 1225 are formed on opposite sides of the cylinder hub 1120 and generally extend from a mid-portion 1224 of the hub 1120 to the first end 1221. Further, the cylinder hub 1120 includes opposing apertures 1226 formed in the cylinder hub 1120 adjacent the second end 1222.

The first end 1221 of the cylinder hub 1120 is coupled to the upper end 1111 of the housing 1110 by tabs 1119 on the housing 1110 engaging shoulders 1228 formed by the cylinder hub 1120. See, for example, FIGS. 59-61, 79A, and 79B. In addition, members 1121 of the housing 1110 are received in slots 1229 of the cylinder hub 1120. In alternative designs, the housing 1110 and cylinder hub 1120 can be formed as a single unit.

Referring now to FIGS. 63-66, the needle hub 1130 includes a main body 1331 with first and second ends 1332 and 1333, and a needle 1336 (hollow or solid) coupled to the main body 1331. The main body 1331 includes opposing wings 1334 formed at the first end 1332 and opposing barbs 1335 at the second end 1333.

The needle hub 1130 is positioned in the interior passage 1223 of the cylinder hub 1120 such that the opposing wings 1334 of the needle hub 1130 extend through the opposing slots 1225 of the cylinder hub 1120. See FIGS. 59, 61, 79B, 80B, 81B, 82B, and 83B. In addition, the opposing barbs 1335 of the needle hub 1130 extend through the opposing apertures 1226 of the cylinder hub 1120 and engage shoulders 1227 formed by the apertures 1226 so that the needle hub 1130 is held in a fixed position relative to the cylinder hub 1120 and the housing 1110. See, for example, FIGS. 59, 61, 79A, 80A, and 81A.

Referring now to FIGS. 67-70, the sleeve 1140 is shown. The sleeve 1140 is preferably cylindrical in shape and includes first and second ends 1441 and 1442 and interior passage 1443. Opposing projections 1444 extend into the passage 1443 adjacent to a shoulder 1445. On the exterior of the sleeve 1140 channels 1446 are formed, as well as railways 1447 with barbs 1448 formed on ends thereof.

The sleeve 1140 is coupled to the housing 1110 such that the housing 1110 can be moved longitudinally with respect to the sleeve 1140. Specifically, the railways 1114 of the housing are received in the channels 1446 of the sleeve 1140. Likewise, the railways 1447 of the sleeve 1140 are received in the channels 1115 of the housing 1110. Barbs 1448 on the railways 1447 of the sleeve 1140 engage projections 1116 in the channels 1115 of the housing 1110 so that the housing 1110 remains slideably coupled to the sleeve 1140 in opposition to the force exerted by the spring 1150 (described further below).

The spring 1150 includes first and second ends 1152 and 1154. See, for example, FIG. 79B. The spring 1150 surrounds a portion of the cylinder hub 1120 and extends within the passage 1443 of the sleeve 1140. The first end 1152 of the spring 1150 is seated on the shoulder 1445 of the sleeve 1140, and the second end 1154 of the spring 1150 engages the opposing wings 1334 of the needle hub 1130 extending through the opposing slots 1225 of the cylinder hub 1120.

The spring 1150 is in a compressed state as shown in FIGS. 79A, 79B, 27A, 27B, 28A, and 28B and therefore applies force against the wings 1334 of the needle hub 1130, biasing the needle hub 1130 in an upward direction. However, barbs 1335 of the main body 1331 of the needle hub 1130 are engaged against shoulders 1227 of the apertures 1226 of the cylinder hub 1120 to retain the needle hub 1130 in place with respect to the cylinder hub 1120. See, for example, FIG. 79A. Likewise, the spring 1150 forces the housing 1110 and the sleeve 1140 apart until barbs 1448 of the sleeve 1140 engage projections 1115 of the housing 1110 to maintain coupling between the housing 1110 and the sleeve 1140.

Figure 71:
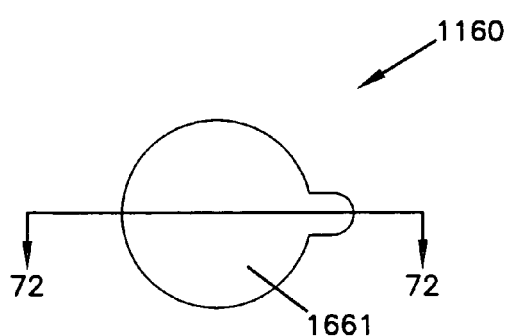
FIG. 71 is a top view of an adhesive portion of the device of FIG. 54.
Figure 72:
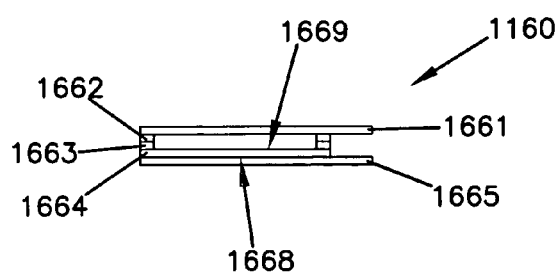
FIG. 72 is a cross-sectional view taken along line 72-72 of the adhesive portion of FIG. 71.
Figure 73:
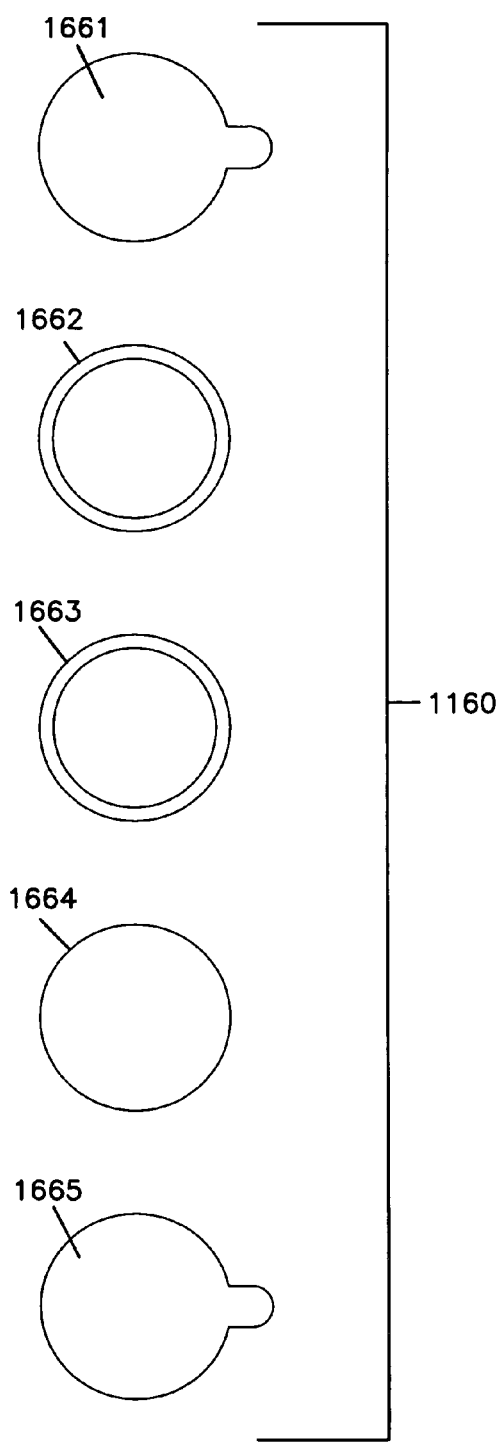
FIG. 73 is an exploded view of the adhesive portion of FIG. 71.

Referring now to FIGS. 71-73, an adhesive portion 1160 is positioned on a surface 1449 at the second end 1442 of the sleeve 1140 (see FIGS. 67 and 70). The surface 1449 preferably acts as a framework that stabilizes the adhesive portion 1160 prior to placement on the patient. In a preferred embodiment shown, the adhesive portion 1160 includes layers 1662, 1663, and 1664, as well as liners 1661 and 1665. Liners 1661 and 1665 also preferably include tabs 1666 and 1667 that allow for removal of the liners 1661 and 1665 as described below.

The adhesive portion 1160 can be coupled to the surface 1449 of sleeve 1140 in a variety of manners. In a preferred embodiment, the liner 1661 is removed, and layer 1662 is coupled to the surface 1449 using an adhesive. In addition, as described further below, in a preferred embodiment a top surface 1669 of layer 1664 and/or a lower end of the infusion device includes an adhesive to couple the infusion device to the adhesive portion 1160 as the infusion device is moved into contact with the adhesive portion. See FIGS. 81A, 81B, and 81C.

In addition, the liner 1665 is preferably removed, and a lower surface 1668 of the layer 1664 includes an adhesive to couple the adhesive portion 1160 to the skin of the patient.

Preferably, the site is loaded into the device 1100 prior to application of the adhesive portion 1160 onto the device 1100, and preferably both liners 1661 and 1665 are removed as described above prior to attachment of the adhesive portion to the sleeve 1140 and coupling of the cap 1170 to the housing 1110. In this manner, the patient preferably does not need to remove any liners prior to application of the adhesive portion 1160 to the skin and introduction of the site into the skin.

Preferably, the layer 1664 does not include any holes, but instead is pierced by the needle 1336 as the needle 1336 is advanced towards the skin, as described further below. This configuration can enhance the fit between the adhesive portion 1160 and the skin of the patient.

In a preferred embodiment, the adhesive portion 1160 includes adhesive on one or more of surfaces 1668 and 1669 to allow the adhesive portion 1160 to be coupled to the sleeve 1140, site, and/or to the skin of the patient. Typical adhesives that can be used on the adhesive portion 1160 include, without limitation, acrylic adhesive, synthetic rubber-based adhesive, acrylate adhesive, and silicone-based adhesive.

In example embodiments, the adhesive portion 1160 includes films with adhesives thereon, such as a Tegaderm™ film manufactured by 3M™ or an IV3000™ film manufactured by Smith & Nephew. For example, in the preferred embodiment shown, the tape layer 1662 is 3M™ 9731 tape, and layers 1663 and 1664 are 3M™ Tegaderm™ p/n 9842.

Referring now to FIGS. 74-76, the cap 1170 is illustrated. The cap 1170 includes a closed first end 1772 and an open second end 1774. The cap 1170 preferably includes an exterior with a knurled surface 1778 to enhance the patient's grip on the cap 1170. In addition, the interior of the cap 1170 includes a threaded portion 1776 positioned adjacent the open second end 1774 so that the threaded portion 1776 can be threaded onto the threaded portion 1113 of the housing 1110 to seal the device 1100. See FIGS. 54, 79A, and 79B.

In a preferred embodiment, a gasket 1122 is provided on the threaded portion 1113 of the housing 1110 to create a seal between the cap 1170 and the housing 1110 as the cap 1170 is threaded onto the housing 1110. See FIGS. 79A and 79B. In this manner, the internal components of the device 1100 (e.g., needle 1336 and site 1800) can be maintained in a substantially sterile state prior to removal of the cap 1170. Further, the cap 1170 can function to maintain the device 1100 in a ship state (i.e., the housing 1110 can not be moved relative to the sleeve 1140) prior to removal of the cap 1170 from the housing 1110.

Figure 104:
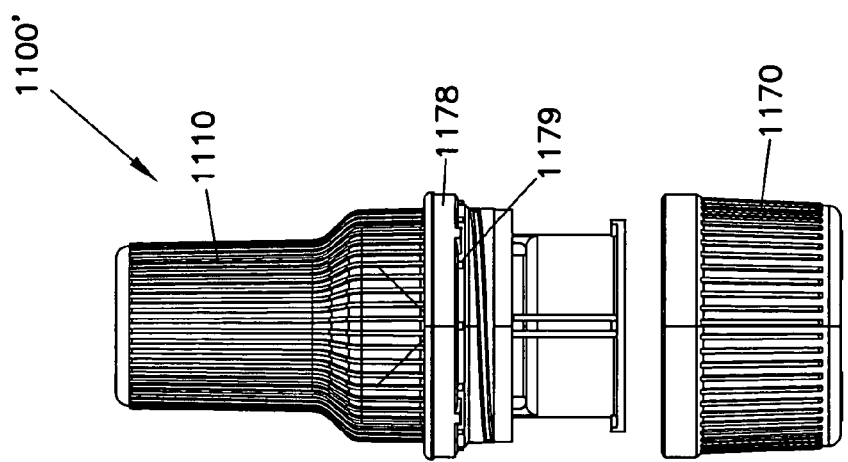
FIG. 104 is a side view of the device of FIG. 103 with the cap uncoupled and the tamper-evident seal having been broken.
Figure 103:
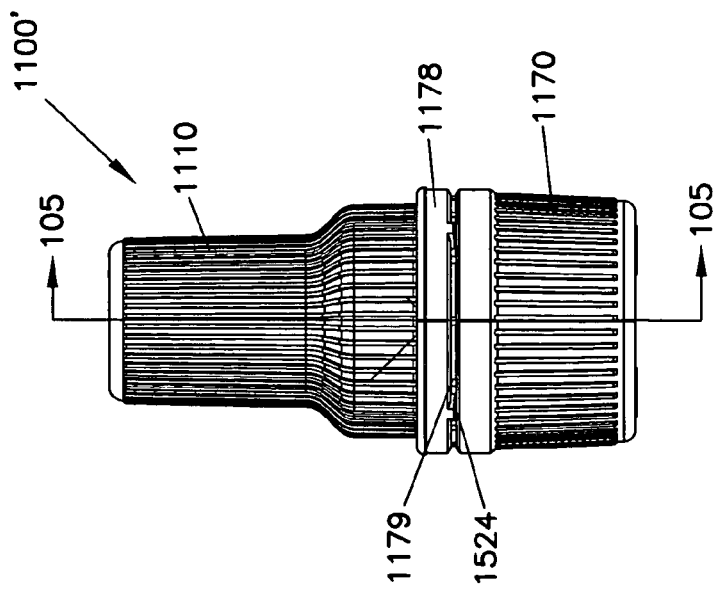
FIG. 103 is a side view of another example embodiment of a device used to introduce a cannula of an infusion device into a patient including a tamper-evident seal made in accordance with the present invention.

In alternative embodiments, the cap 1170 and/or housing 1110 can be formed to provide a tamper-evident seal so that the patient can determine when the cap 1170 has been previously uncoupled from the housing 1110. For example, in an alternative embodiment of the device 1100' shown in FIGS. 103-105, a tamper-evident band 1178 is shown. The band 1178 includes tabs 1179 that are coupled to the cap 1170 as shown in FIG. 103. As the cap 1170 is removed from the housing 1110 (i.e., threads 1514 on cap 1170 are unthreaded from threads 1512 on housing 1110), the tabs 1179 break away from the cap 1170, and the seal 1178 remains coupled to the housing 1110, as shown in FIG. 104. If the cap 1170 is later threaded back onto the device 1100', the breaks between the tabs 1179 and the cap 1170 are evident, allowing the patient to identify that the cap 1170 of the device 1100' has been previously removed.

The cap 1170 and band 1178 can be placed on the device 1100' during manufacturing as a single unit. For example, as shown in FIG. 105, the cap 1170 and band 1178 can be pushed onto the device 1100' (note that threads 1512 and 1514 can be rounded to allow the cap 1170 to be pressed onto the device 1100') so that portion 1520 of the band 1178 passes over and engages shoulder 1522 of the housing 1110 to retain the band 1178 on the housing 1110 when the cap 1170 is unthreaded and tabs 1179 are broken. In addition, notches 1524 formed periodically along the band 1178 prevent the cap 1170 from bottoming out against the band 1178 as the cap 1170 and band 1178 are pushed onto the device 1100' so that the tabs 1179 remain intact. A portion 1502 extending along an interior circumference of the cap 1170 can also be formed to engage the outer surface of the housing 1110 to create a seal between the housing 1110 and the cap 1170.

It can be desirable to provide a tamper-evident seal, for example, so that the patient can assure that the device 1100' is has not been previously opened and is sterile prior to use. Other methods of indicating tampering can also be used.

As previously noted, device 1100 can be used to insert a cannula 1806 of an infusion device, such as site 1800, into the subcutaneous layer of skin of a patient. In preferred embodiments, the site 1800 is configured in a manner similar to sites 100 or 450 described above.

Figure 79B:
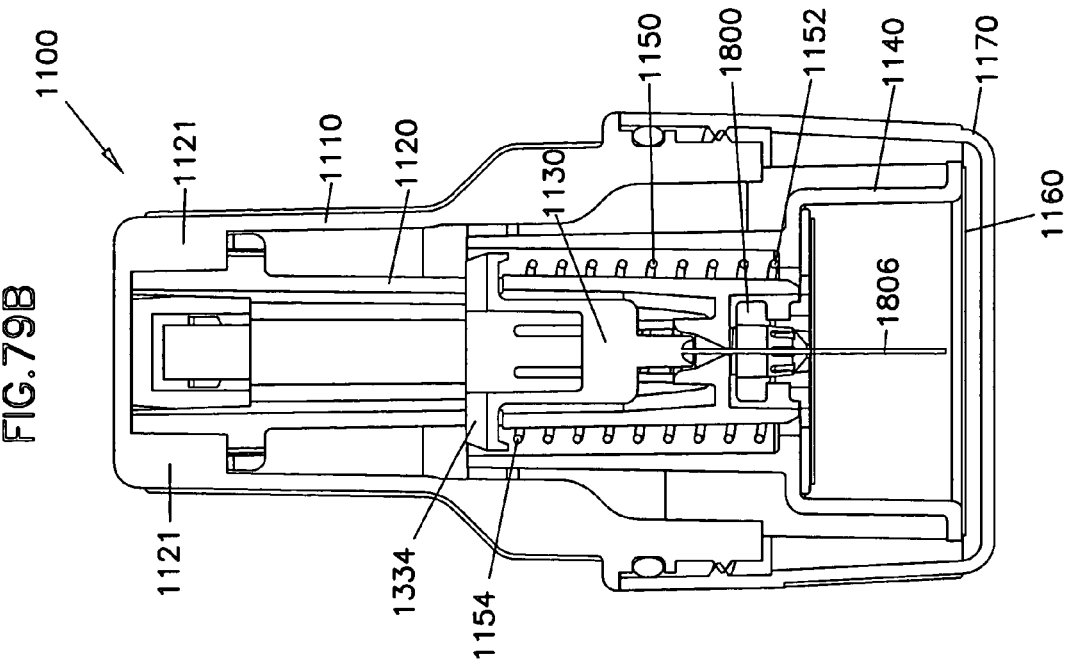
FIG. 79B is a cross-sectional view taken along line 79B-79B of the device of FIG. 54 in the ship state.
Figure 79A:
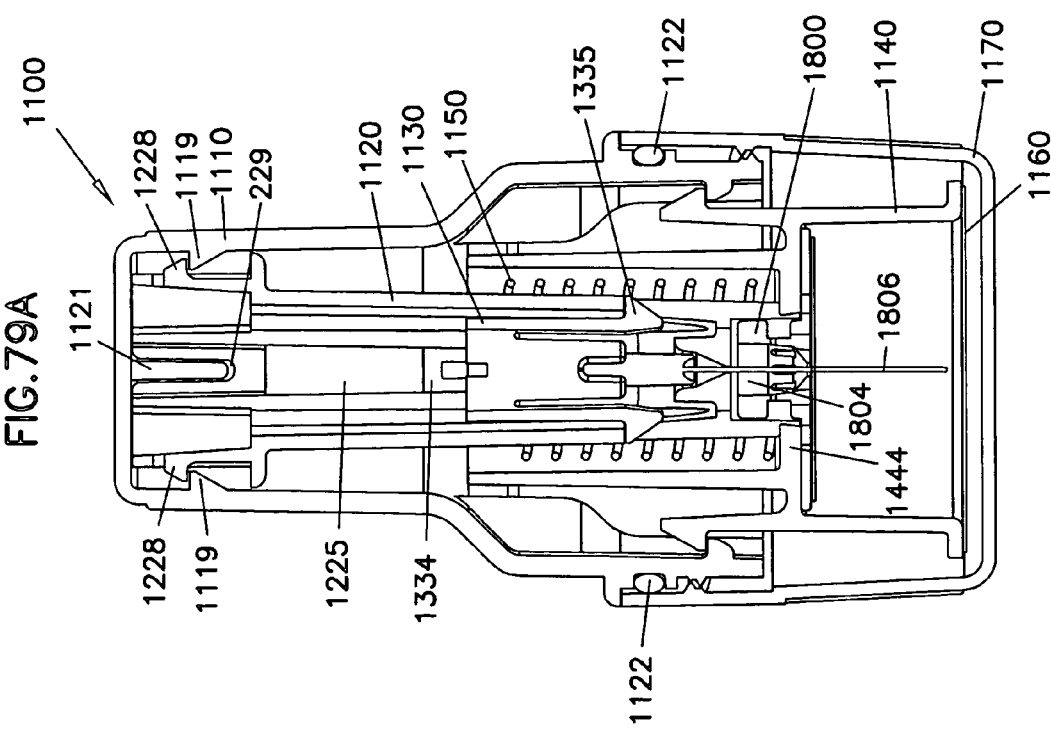
FIG. 79A is a cross-sectional view taken along line 79A-79A of the device of FIG. 54 in a ship state.
Figure 82A:
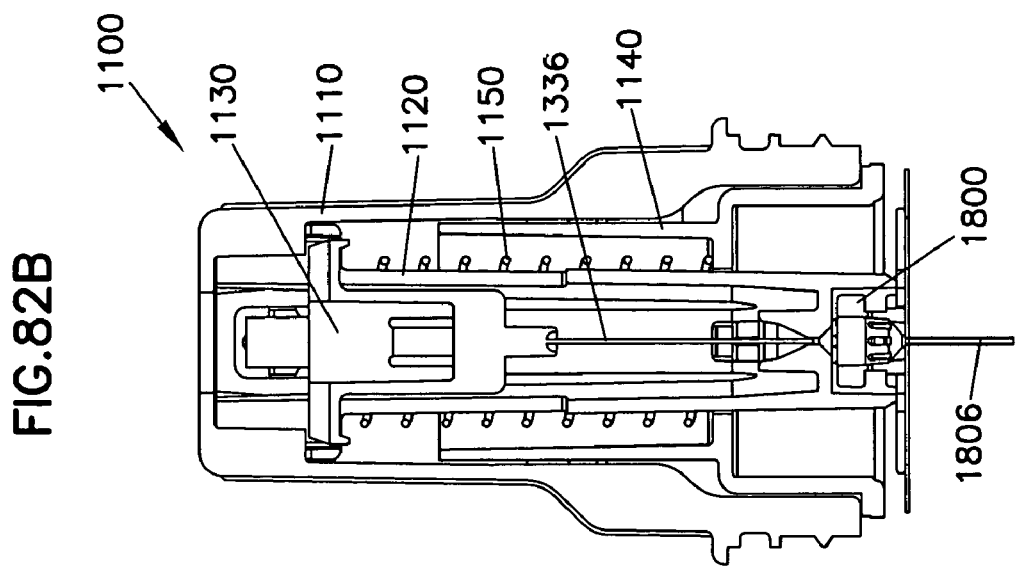
FIG. 82A is a cross-sectional view of the device of FIG. 81A with the needle hub retracted.
Figure 82B:
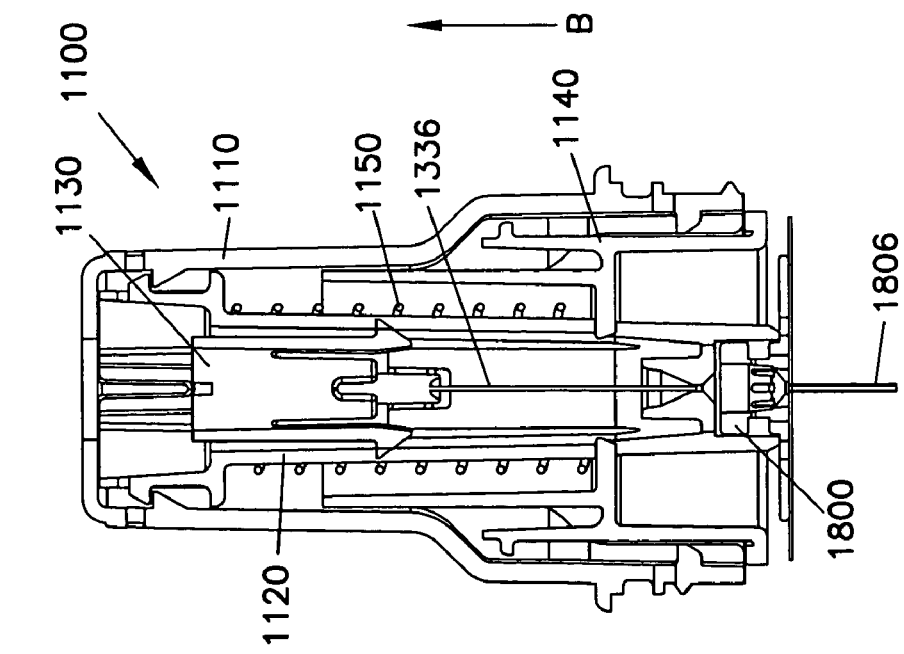
FIG. 82B is a cross-sectional view of the device of FIG. 81B with the needle hub retracted.
Figure 85A:
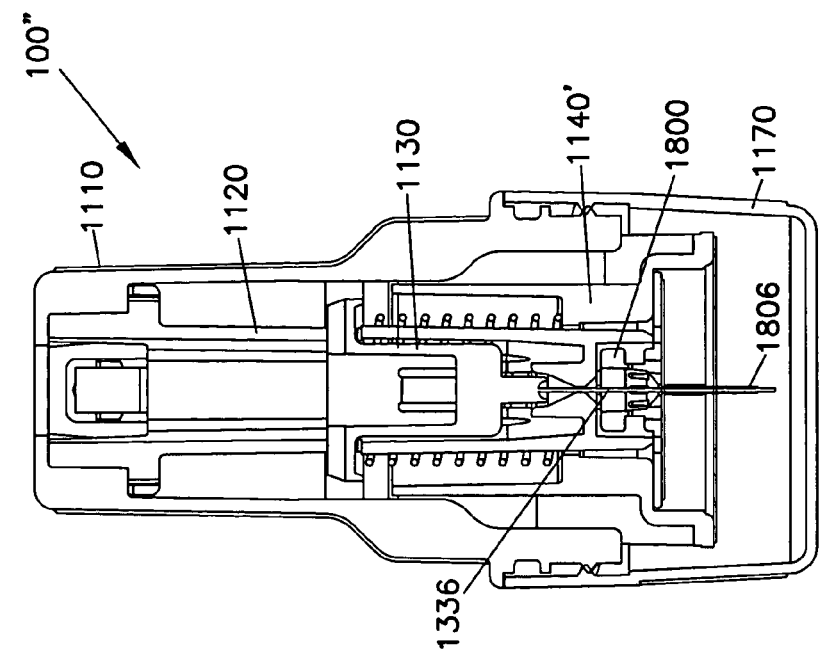
FIG. 85A is a cross-sectional view of another example embodiment of a device used to introduce an infusion device into a patient in a ship state made in accordance with the present invention.
Figure 85B:
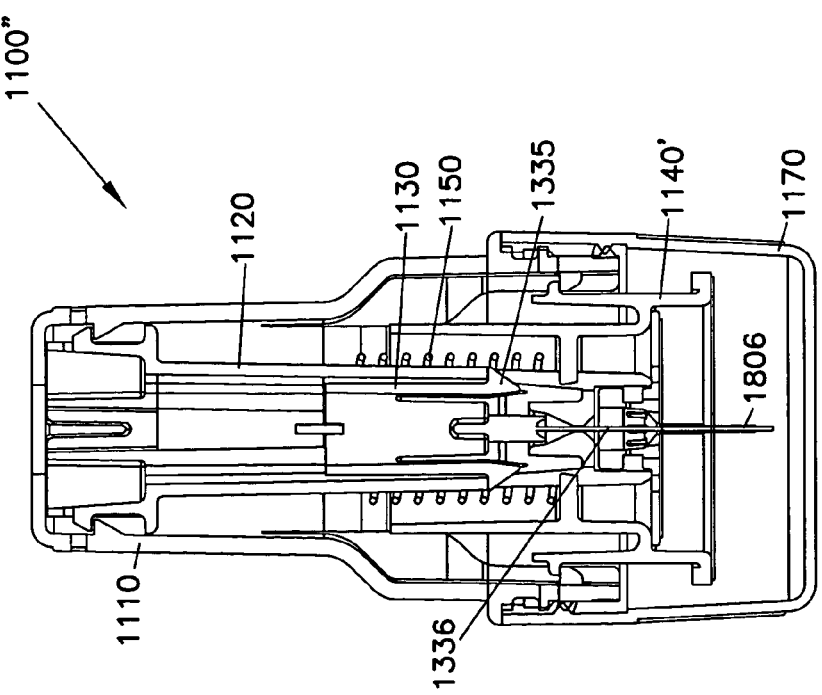
FIG. 85B is a cross-sectional view along a perpendicular plane of the device of FIG. 85A.

Referring now to FIGS. 54 and 67-83, the device 1100 is illustrated in various states of use. As shown in FIGS. 54, 79A, and 79B, the device 1100 is in a ship state prior to use. As shown in FIGS. 77, 80A, and 80B, the device 1100 is in a delivery state ready to deliver the cannula of an infusion device into the skin of the patient. As shown in FIGS. 78, 81A, 81B, and 81C the device 1100 is in a trigger state, or the state at which the needle 1336 and the cannula of the site 1800 have been fully inserted into the subcutaneous layer of skin of the patient, and the needle hub 1130 and associated needle 1336 are about to be retracted. As shown in FIGS. 82A and 82B, the device 1100 is in a retracted state with the needle hub 1130 and associated needle 1336 having been retracted into the device 1100. As shown in FIGS. 83A and 83B, the device 1100 is in a fully retracted state with the housing 1110 and sleeve 1140 returned to an uncompressed position relative to one another.

An example method of use of the device 1100 is as follows. The device 1100 is provided to a patient with the cap 1170 coupled to the housing 1110, as shown in FIGS. 54, 79A, and 79B. Preferably, the site 1800 has been previously loaded (i.e., preloaded) into the device 1100 during, for example, the manufacturing process for the device 1100.

For example, the site 1800 can be preloaded by introducing the site 1800 onto the needle 1336. More particularly, a diaphragm of the site 1800 is positioned on the needle 1336, and the site 1800 is moved further onto the needle 1336 so that the needle 1336 extends through the cannula 1806. With the site 1800 positioned on the needle 1336, the cap 1170 can be coupled to the device 1100.

Referring back to the method of using the device 1100, the cap 1170 is then unthreaded from the housing 1110, and the sleeve 1140 of the device 1100 is positioned so that the adhesive portion 1160 (i.e., surface 1668) contacts the skin 1900 of the patient. See FIGS. 77, 80A, and 80B.

Next, in the illustrated preferred embodiment, the patient applies pressure to the upper end 1111 of the housing 1110 to move the housing 1110 and associated structures including the cylinder hub 1120 and needle hub 1130 (including needle 1336 and site 1800) in a direction A with respect to the sleeve 1140 and toward the skin 1900 of the patient. As the needle 1336 of the needle hub 1130 and associated site 1800 are moved in the direction A, the needle 1336 and the cannula 1806 of the site 1800 are introduced into the skin 1900 of the patient. In addition, as the needle hub 1130 is moved toward the sleeve 1140, the spring 1150 is further compressed.

Once the needle 1336 and cannula 1806 of the site 1800 have been fully inserted into the skin 1900, the device 1100 is in a trigger state, as illustrated in FIGS. 78, 81A, 81B, and 81C. In this state, the barbs 1335 that couple the needle hub 1130 to the cylinder hub 1120 are biased inwardly through contact with the projections 1444 formed by the sleeve 1140.

As the housing 1110, cylinder hub 1120, and needle hub 1130 are displaced further in the direction A, it is preferable that the needle hub 1130 is positioned so that a lower portion of the site 1800 travels slightly beyond the second end 1442 of the sleeve 1140 as shown in FIG. 81C. This "over-travel" assures that the adhesive portion 1160 is properly sheared away from the surface 1449 of the sleeve 1140 and allows for the coupling of the site 1800 to the adhesive portion 1160.

For example, in preferred embodiments, the lower portion of the site 1800 travels beyond the second end 1442 of the sleeve 1140 by between 50 to 100 thousandths of an inch, more preferably approximately 70 thousandths of an inch. Adhesive can be provided on the adhesive portion 1160 of the device 1100 and/or the site 1800 to couple the site 1800 to the adhesive portion 1160.

In addition, as the housing 1110, cylinder hub 1120, and needle hub 1130 are displaced further in the direction A as described above, barbs 1335 of the needle hub 1130 are forced inwardly by the projections 1444 of the sleeve 1140, and the barbs 1335 are thereby uncoupled from engagement with the cylinder hub 1120. Once the barbs 1335 of the needle hub 1130 are released from the cylinder hub 1120, the needle hub 1130 is free to move longitudinally within the passage 1223 of the cylinder hub 1120 in a direction B opposite to that of the direction A. The spring 1150, which has been compressed through the movement of the housing 1110 in the direction A, propels the needle hub 1130 and associated needle 1336 in the direction B up through the cylinder hub 1120 into the upper end 1111 of the housing 1110, while the site 1800 and associated cannula 1806 are held on the skin 1900 of the patient, as shown in FIGS. 82A and 82B.

Once the patient removes pressure from the upper end 1111 of the housing 1110, the spring 1150 causes the housing 1110 and cylinder hub 1120 to move in the direction B as shown in FIGS. 83A and 83B to a fully retracted state.

Finally, the sleeve 1140 is removed from contact with the skin 1900, and the cap 1170 can be replaced onto the threaded portion 1113 of the housing 1110 of the device 1100. Subsequently, the device 1100 can be discarded.

Many alternative designs for the device can be provided. For example, in FIG. 84 a portion of an alternative device is shown including cylinder hub 1120' and needle hub 1130'. The cylinder hub 1120' and needle hub 1130' are similar to cylinder hub 1120 and needle hub 1130 described above, except that the cylinder hub 1120' includes projections 1129 formed near the first end 1221 of the cylinder hub 1120', and the needle hub 1130' includes barbs 1139 formed on the first end 1332. The barbs 1139 are configured to ride inside the interior passage 1223 of the cylinder hub 1120' during retraction of the needle 1336 in the direction B until the barbs 1139 extend beyond the projections 1129 of the cylinder hub 1120'. Once this occurs, the barbs 1139 expand outward slightly. In this configuration as shown in FIG. 84, the barbs 1139 prevent the needle hub 1130' and associated needle 1336 from being moved back in the direction A. In this manner, the barbs 1129 lock the needle hub 1130' in the retracted position. This configuration can be beneficial, used separately or in conjunction with the force of the spring 1150 forcing the needle hub 1130' in the direction B, to further reduce the possibility of inadvertent exposure to the needle 1336 after retraction.

According to another alternative embodiment, a device 1100" is illustrated in FIGS. 85-91. Device 1100" is similar to device 1100 described above, except that the sleeve (e.g., sleeve 1140) is replaced with a trigger 1140'. In device 1100", the trigger 1140' (see FIGS. 88-91) does not function as sleeve 1140 to shroud the needle 1336 prior to insertion, but instead trigger 1140' functions to cause retraction of the needle 1336 upon full insertion, as described further below.

Figure 86B:
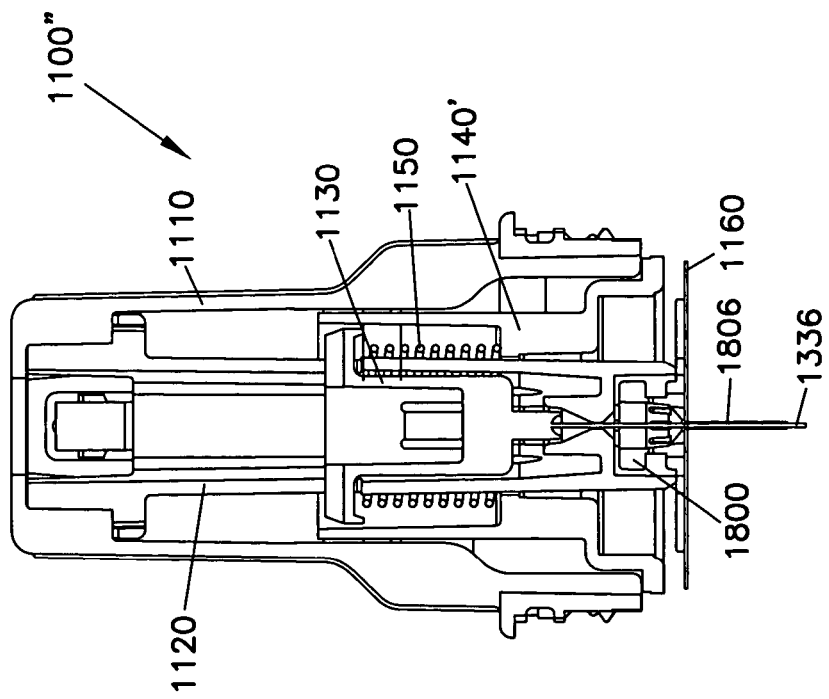
FIG. 86B is a cross-sectional view of the device of FIG. 85B in the delivery state.
Figure 86A:
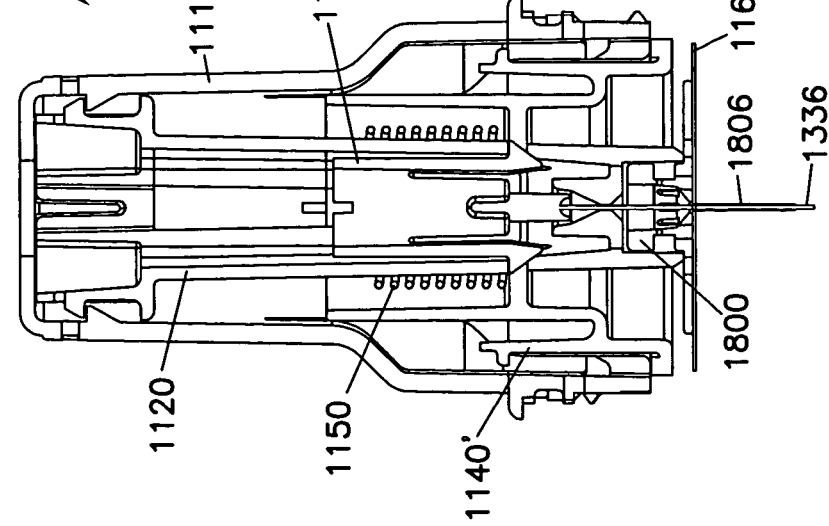
FIG. 86A is a cross-sectional view of the device of FIG. 85A in a delivery state.
Figure 97:
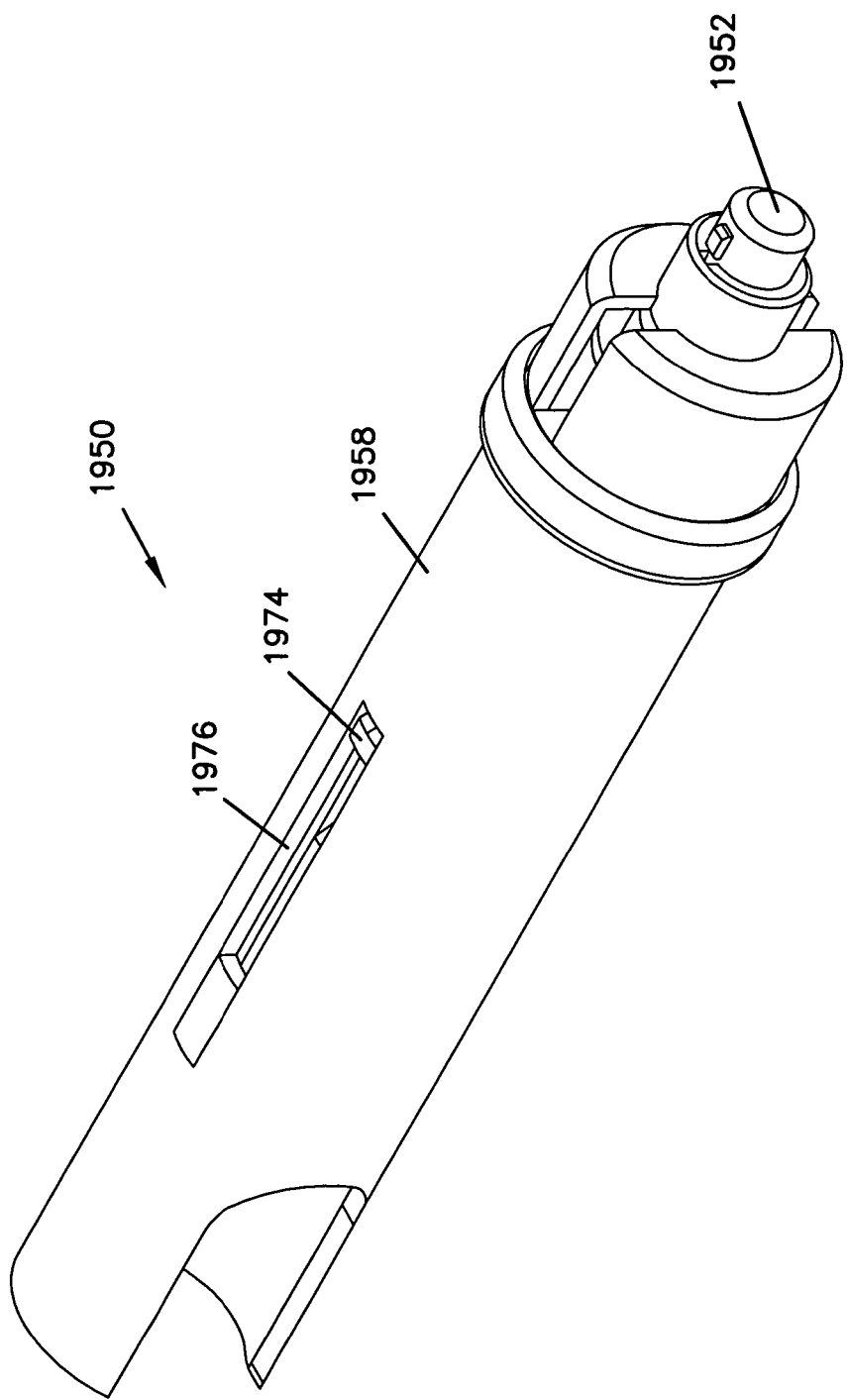
FIG. 97 is a perspective view of another example embodiment of a device used to introduce an infusion device into a patient made in accordance with the present invention.
Figure 98:
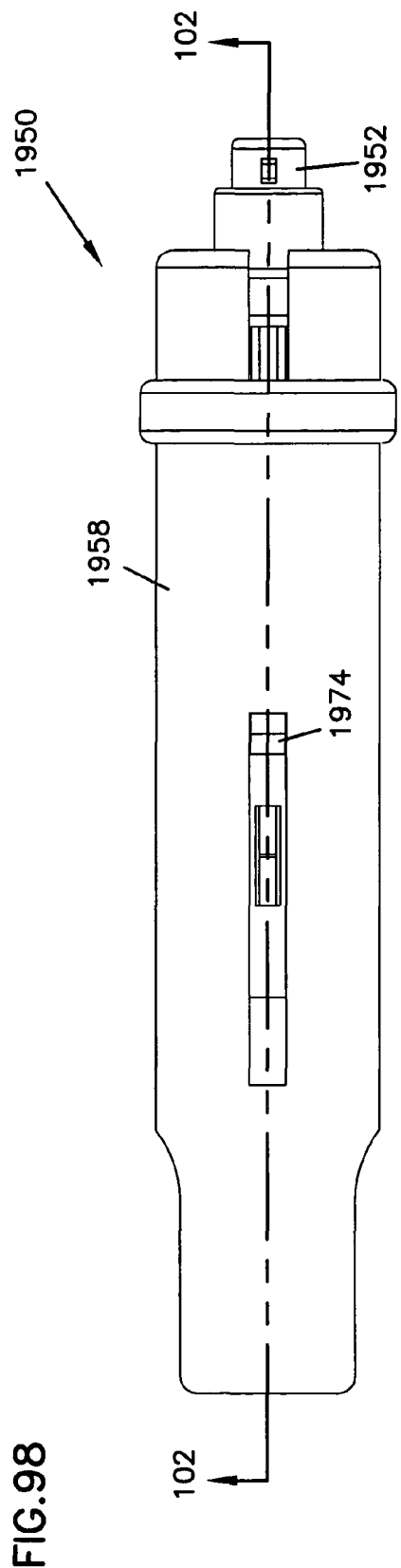
FIG. 98 is a side view of the device of FIG. 97.
Figure 99:
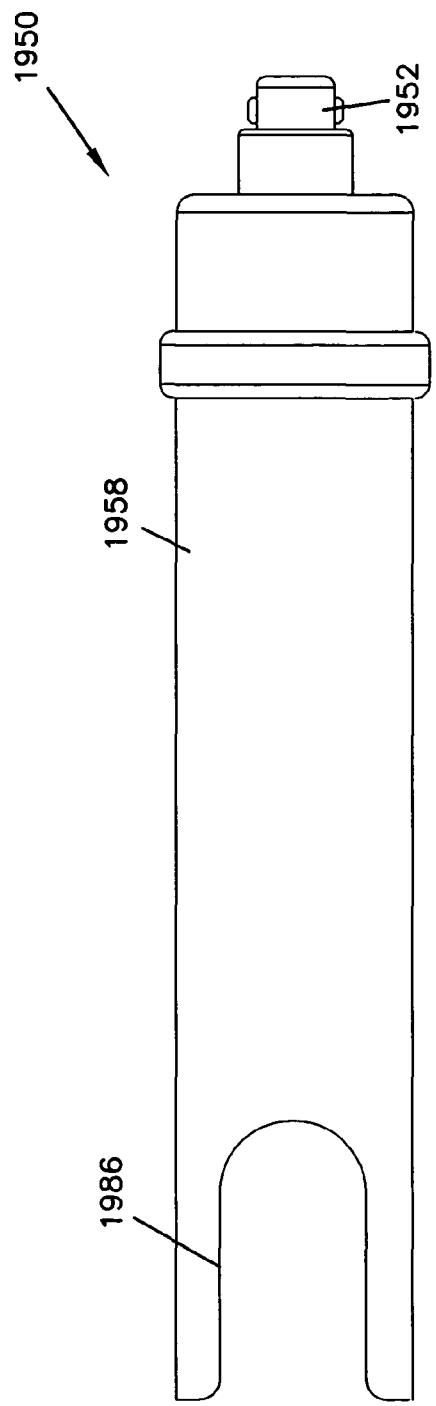
FIG. 99 is another side view of the device of FIG. 97.

In this embodiment of device 1100", once the cap 1170 has been removed, needle 1336 is exposed as shown in FIGS. 86A and 86B. In this configuration, instead of moving the housing 1110, cylinder hub 1120, and needle hub 1130 longitudinally with respect to the housing, the patient simply inserts the needle 1336 and associated cannula 1806 of the site into the skin by grasping the housing 1110 and introducing the exposed needle 1336 into the skin.

As the needle 1336 and cannula 1806 reaches full insertion, the trigger 1140' contacts the skin and thereby causes the needle hub 1130 including the needle 1336 to be retracted into the housing 1110, leaving the site 1800 in place on the skin. In the illustrated embodiment, the trigger 1140' is automatic, in that the trigger 1140' is configured to cause barbs 1335 of the needle hub 1130 to be displace inwardly to release the needle hub 1130 from the cylinder hub 1120, and the spring 1150 can thereupon move the needle hub 1130 and associated needle 1336 in the direction B into an upper portion of the housing 1110 as shown in FIGS. 87A and 87B.

In alternative embodiments, the trigger 1140' can be configured to be manually actuated by the patient to cause retraction of the needle hub 1130 and associated needle 1336 once the cannula 1806 has been fully inserted.

Referring now to FIGS. 92-96, another embodiment of a device 1100''' is shown. The device 1100''' is a manual device in that the device 1100''' includes only a housing 1110', needle 1336, and cap (not shown) that can be threaded onto the housing 1110'. Preferably, a site (not shown) can be preloaded onto the needle 1336 and the cap placed on the housing 1110' to create a sterile environment prior to use. To use device 1100''', the patient preferably removes the cap from the housing 1110' and, holding the housing 1110' inserts the needle and associated cannula of the site into the skin. Once the cannula is completely inserted, the patient moves the housing 1110' in the opposite direction to remove the needle from the skin while leaving the site in place. Finally, the patient preferably reapplies the cap to the housing 1110' to reduce the chance for further inadvertent exposure to the needle 1336. The device 1100''' can then be discarded or reused as desired.

Referring now to FIGS. 97-102, another example embodiment of a device 1950 for assisting in the introduction of a site 1970 is shown. The device 1950 differs from the device 1100. For example, while the device 1100 can be manually driven by the patient to insert the needle and cannula of the site into the skin, the device 1950 is automated in that a spring 1960 is used to drive the needle and cannula of the site into the skin of the patient.

The device 1950 includes a housing 1958, cap 1952, lock member 1962, needle hub 1965, main body 1980, retainer body 1978, and sleeve 1982. Also included are the first spring 1960 and a second spring 1966.

The device 1950 functions as follows. The lock member 1962, needle hub 1964, and retainer body 1978 are moveable longitudinally with respect to the housing 1958 and sleeve 1982 of the device 1950. The lock member 1962 is positioned so that needle 1968 of the needle hub 1965 is accessible from open end 1984 of the device 1950. The site 1970 can then be loaded onto the needle 1968 by threading the cannula of the site 1970 onto the needle 1968. Openings 1986 are formed by the housing 1958 to accommodate sites 1970 of various sizes (e.g., wings formed on sites).

Figure 102:
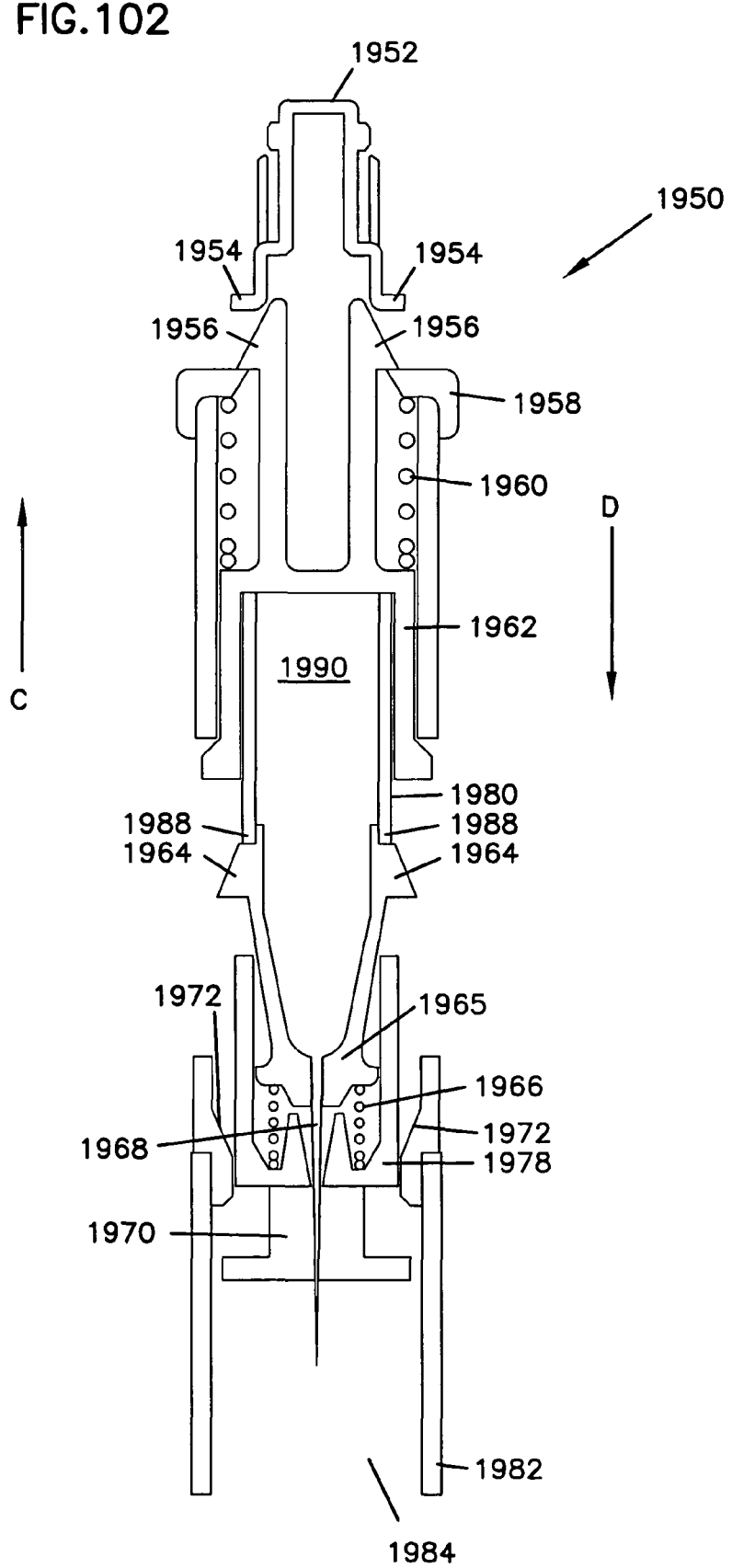
FIG. 102 is a cross-sectional view taken along line 102-102 of the device of FIG. 98.

Once the site 1970 has been loaded onto the needle 1968, the lock member 1962 is moved in a direction C by the patient using projections 1974 that are accessible through slot 1976 of housing 1958 until barbs 1956 of the lock member 1962 engage an outer surface of the housing 1958, as shown in FIG. 102. In this position, the device 1950 is ready to insert the site 1970 into the skin of the patient.

Next, the sleeve 1982 of the device 1950 is placed against the skin of the patient. To initiate insertion of the site 1970, the cap 1952 is pressed by the patient. Once pressed, shoulders 1954 on an opposite end of the cap 1952 engage and push the barbs 1956 of the lock member 1962 toward one another to disengage the barbs 1956 from the housing 1958. When the barbs 1956 clear the housing 1958, the lock member 1962, main body 1980, needle hub 1965, retainer body 1978, and associated site 1970 are moved by the first spring 1960 a the direction D.

The device 1950 continues to move the site 1970 towards the skin, thereby introducing the needle 1968 and cannula of the site 1970 into the skin. As the cannula of the site 1970 is fully inserted into the skin, barbs 1964 of the needle hub 1965 engage ramped surfaces 1972 of the sleeve 1982, causing the barbs 1964 to be forced toward one another. When the cannula of the site 1970 is fully inserted into the skin, the barbs 1964 have been forced inwardly by the surfaces 1972 sufficiently to clear ends 1988 of the main body 1980, and the second spring 1966 moves the needle hub 1965 in the direction C into a passage 1990 formed by the main body 1980.

As the needle hub 1965 is moved by the second spring 1966 into the main body 1980, the needle 1968 is removed from the site 1970, leaving the site 1970 in place on the skin. In addition, the retainer body 1978 remains in a position adjacent the open end 1984 of the sleeve 1982 so that once the device 1950 is removed from the skin of the patient, the retainer body 1978 protects the patient from further contact with the needle 1968.

Infusion devices made in accordance with the principles described herein can be advantageous for various reasons. For example, the set can be coupled in various selectable rotational orientations with respect to the site. In some embodiments, a plurality of orientations can be provided. This allows a patient to rotationally orient the set (and associated tube coupled to the set) as desired so that the tube can extend, for example, towards an infusion pump regardless of where the site is placed on the body of the patient.

In addition, the set and associated tube can be removed from the site multiple times while leaving the site on the skin. This can be desirable if the patient wants to reorient the set with respect to the site, or if the patient wants to remove the set from the site for a period of time, such as if the patient wishes to shower and then replace the set onto the site. Further, the site is preferably configured to have a low profile to be unobtrusive to the patient.

The engagement of the set with the site and sliding action of the set from the unlocked to locked position can also be advantageous in that a patient can preferably accomplish orientation and coupling of the set to the site using a single hand. This can be preferable, for example, if the site has been placed on a portion of the body of the patient that is not easily reached using two hands, or cannot easily be seen by the patient (e.g., if the site is placed on the back of the patient).

Further, the configuration of the set functions to protect the patient from inadvertent contact with the hollow needle (e.g., needles 214 and 411) used to pierce the diaphragm and deliver the substance to the site. For example, the outer arms 220 and 222 and the inner arms 226 and 228 of the first member 210 of the set 200 generally surround the needle 214 and function to reduce the chance that the patient will inadvertently contact the needle.

Also, the configuration of the diaphragm in the site can be preferable in that a single diaphragm can function to both allow introduction of the cannula of the site into the body using one needle, as well as coupling of the set with the site using a second needle. In addition, the diaphragm can preferably be held within the site through frictional engagement between the diaphragm and the site without requiring additional structure to retain the diaphragm in the site.

Although examples of infusion devices have been described herein, various modifications can be made to the devices. For example, as noted above the member 120 of the site 100 and the aperture 270 of the set 200 can be formed in a variety of shapes to allow the set 200 to be oriented in multiple positions with respect to the site 100. In addition, a retaining member can be fitted over the open top of the member 120 to further retain the diaphragm 150 in position in the cavity 121.

In another alternative embodiment, the second member 250 of the site 200 can be constructed to include a cover portion extending from the main body 260 so that when the set 200 is moved to the locked position the cover extends over the closed end 154 of the diaphragm 150 to reduce exposure of the set and site to outside contaminants.

Devices used to insert infusion devices made in accordance with the principles described herein can be advantageous for various reasons. For example, each device can provide ease in placement of the site on the skin, preferably allowing the user to place the site with the device where desired on the body using a single hand to operate the device.

Further, several embodiments disclosed herein include structures that cover or hide the needle prior to insertion of the site, and also cause the needle to be retracted into the device after insertion to protect against inadvertent contact with the needle.

In addition, several embodiments of the devices disclosed herein can automatically retract the needle while leaving the site placed on the skin, thereby reducing the patient's contact with the exposed needle. Preferably, this retraction is automatic in that once the device reaches the trigger state there is no further action required by the patient to cause the needle to be retracted. The automatic retraction of the needle also limits the dwell time of the needle in the patient, increasing comfort for the patient.

In addition, the action of inserting the needle into position on the skin using the devices disclosed herein can function to hold the site on the surface of the skin during needle retraction. This can assist in adherence of the adhesive portion to the skin and reduce the chances of separation between the adhesive portion and site and the skin during needle retraction.

In addition, the housing and cap of several of embodiments of the devices disclosed herein allow the various components of the devices including the needle and infusion device to be delivered to the patient in a self-contained, sterile environment prior to use. The configuration further minimizes the need for packaging surrounding the devices, reducing manufacturing cost and increasing ease in use of the devices. The configuration also allows the housing and cap to protect and maintain the site on the needle of the device. The configuration and disposable nature of the devices further allow ease in discarding of the devices after use.

Also, the configuration of several embodiments of the devices disclosed herein can allow the site to be preloaded into the device, thereby providing ease of use for the patient and reducing the patient's exposure to the needle. For example, single-use embodiments disclosed herein preferably do not require that the patient load the site into the device prior to insertion, but instead provide the device with the site preloaded.

Some embodiments of the devices allow for both automatic delivery of the site and withdrawal of the needle, thereby automating the entire introduction process for the patient.

While single use devices are preferred, reusable devices wherein the needle retracts but can be reloaded are also anticipated.

The above specification, examples and data provide a complete description of the manufacture and of the invention. Since many embodiments of the invention can be made without departing from the spirit and scope of the invention, the invention resides in the claims hereinafter appended.

What is claimed is:

1. A method for introducing an infusion device into a subcutaneous layer of skin of a patient, comprising:
providing an infusion device preloaded onto a needle of an insertion device so that the needle extends through a cannula of the infusion device, and a sleeve coupled to a housing of the insertion device that hides the needle prior to retraction, wherein the needle is coupled to the housing of the insertion device so that, as the housing is moved relative to the sleeve, the needle is moved relative to the sleeve;

positioning the insertion device adjacent to the skin of the patient;

allowing a patient to manually introduce the cannula of the infusion device into a subcutaneous layer of skin of the patient by manually moving the housing and the needle of the insertion device relative to the sleeve from a retracted position to an extended position, wherein manually moving the needle is accomplished by allowing the patient to move the housing relative to the sleeve towards the skin of the patient; and upon full manual insertion of the cannula by the insertion device and the insertion device reaching a trigger state, automatically moving the needle of the insertion device from the extended position to the retracted position while leaving the sleeve in contact with the skin of the patient.

2. The method of claim 1, wherein the step of providing an infusion device further comprises coupling a cap to the insertion device.

3. The method of claim 2, further comprising removing the cap prior to introducing the cannula into the subcutaneous layer of skin of the patient.

4. The method of claim 1, wherein the infusion device includes a site having the cannula, and a set, and the method further comprises coupling the set to the site of the infusion device positioned on the skin of the patient.

5. The method of claim 4, wherein the step of coupling the set to the site of the infusion device further comprises:

positioning the set in an unlocked position over the site;

positioning the set onto the site; and moving the set from the unlocked position to a locked position to couple the set to the site and to introduce a needle of the set into a reservoir defined by the site.

6. The method of claim 5, wherein the step of moving further comprises sliding a first member of the set relative to a second member of the set to move the set from the unlocked position to the locked position.

7. The method of claim 5, further comprising moving the set from the locked position to the unlocked position.

8. The method of claim 7, further comprising:

reorienting the set rotationally relative to the site; and moving the set from the unlocked position to the locked position to recouple the set to the site and to reintroduce a needle of the set into a reservoir defined by the site.

* * * * *